(12) United States Patent
Olandt et al.

(10) Patent No.: US 6,939,698 B2
(45) Date of Patent: Sep. 6, 2005

(54) 33945, A HUMAN GLYCOSYLTRANSFERASE FAMILY MEMBER AND USES THEREFOR

(75) Inventors: Peter J. Olandt, East Boston, MA (US); Rachel E. Meyers, Newton, MA (US); Katherine M. Galvin, Jamaica Plain, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/074,527

(22) Filed: Feb. 12, 2002

(65) Prior Publication Data

US 2002/0142426 A1 Oct. 3, 2002

Related U.S. Application Data

(60) Provisional application No. 60/269,202, filed on Feb. 15, 2001.

(51) Int. Cl.$^7$ .......................... C12P 21/06; C12N 9/00; C12N 9/10; C07H 21/04
(52) U.S. Cl. .............................. 435/193; 435/4; 435/6; 435/18; 435/41; 435/69.1; 435/183; 435/252.3; 435/320.1; 435/325; 536/23.2; 536/23.4; 536/23.5
(58) Field of Search .............................. 435/4, 6, 69.1, 435/183, 193, 194, 252.3, 320.1, 325; 536/23.2–23.7; 530/350

(56) References Cited

U.S. PATENT DOCUMENTS

| | | | |
|---|---|---|---|
| 5,871,990 A | | 2/1999 | Clausen et al. |
| 5,910,570 A | | 6/1999 | Elhammer et al. |
| 2003/0186850 A1 | * | 10/2003 | Clausen et al. .................. 514/8 |

FOREIGN PATENT DOCUMENTS

| | | | |
|---|---|---|---|
| WO | WO 00/55351 A1 | | 9/2000 |
| WO | WO 02/46426 | * | 6/2002 |

OTHER PUBLICATIONS

White, Thayer et al. "Purification and cDNA Cloning of a Human UDP–N–acetyla–α–D–galactosamine:polypeptide N–Acetylgalactosaminyltransferase" *The Journal of Biological Chemistry* vol. 270, No. 41, (Oct. 13, 1995) pp. 24156–24165.

Strausberg, R., "*Homo sapiens*, Similar to hypothetical protein FLJ21212, clone MGC:24384 IMAGE:4064736; mRNA, complete cds.", Sep. 10, 2001 (sequence) GenBank [online] Bethesda, MD, USA: National Center for Biotechnology information [retrieved on Aug. 19, 2002]. Retrieved from the Internet: URL: http://www.ncbi.nlm.nih.gov/>. GenBank Accession No. BC013945.

Kawabata, A., et al., "*Homo sapiens* cDNA: FLJ21212 fis, clone COL00502" Sep. 29, 2000 (sequence) GenBank [online] Bethesda, MD, USA: National Center for Biotechnology Information [retrieved on Aug. 19, 2002]. Retrieved from the Internet: URL: http://www.ncbi.nlm.nih.gov/>. GenBank Accession No. AK024865.

Osada, N., et. al., "*Macaca fascicularis* brain cDNA, clone:QnpA–17439" Sep. 20, 2000 (sequence) GenBank [online] Bethesda, MD, USA: National Center for Biotechnology Information [retrieved on Aug. 19, 2002]. Retrieved from the Internet: URL: http://www.ncbi.nlm.nih.gov/>. GenBank Accession No. AB048901.

Hagen, F.K., et. al., "polypeptide GalNAc transferase–T4 [Mus musculus]." May 26, 1997 (sequence) GenBank [online] Bethesda, MD, USA: National Center for Biotechnology Information [retrieved on Aug. 19, 2002]. Retrieved from the Internet: URL: http://www.ncbi.nlm.nih.gov/>. GenBank Accession No. AAB58301.

* cited by examiner

Primary Examiner—Manjunath N. Rao
(74) Attorney, Agent, or Firm—Millennium Pharmaceuticals, Inc.

(57) ABSTRACT

The invention provides isolated nucleic acids molecules, designated 33945 nucleic acid molecules, which encode novel glycosyltransferase family members. The invention also provides antisense nucleic acid molecules, recombinant expression vectors containing 33945 nucleic acid molecules, host cells into which the expression vectors have been introduced, and nonhuman transgenic animals in which a 33945 gene has been introduced or disrupted. The invention still further provides isolated 33945 proteins, fusion proteins, antigenic peptides and anti-33945 antibodies. Diagnostic and therapeutic methods utilizing compositions of the invention are also provided.

19 Claims, 1 Drawing Sheet

SEQUENCE LISTING

```
<160> NUMBER OF SEQ ID NOS: 9

<210> SEQ ID NO 1
<211> LENGTH: 2850
<212> TYPE: DNA
<213> ORGANISM: homo sapiens
<220> FEATURE:
<221> NAME/KEY: CDS
<222> LOCATION: (81)...(1826)

<400> SEQUENCE: 1
ccggctcggt accactataa cggccgccag tgtgctggaa ttcgcccttg cgcagatcgc      60
tggctgcagt tggcgggcgc atg tgg ggg cgc acg gcg cgg cgg cgc tgc ccg    113
                      Met Trp Gly Arg Thr Ala Arg Arg Arg Cys Pro
                       1               5                  10
```

-continued

```
cgg gaa ctg cgg cgc ggc cgg gag gcg ctg ttg gtg ctc ctg gcg cta      161
Arg Glu Leu Arg Arg Gly Arg Glu Ala Leu Leu Val Leu Leu Ala Leu
         15                  20                  25 ctg gcg ttg gcc ggg ctg ggc tcg gtg ctg cgg gcg cag cgt ggg gcc      209
Leu Ala Leu Ala Gly Leu Gly Ser Val Leu Arg Ala Gln Arg Gly Ala
             30                  35                  40 ggg gcc ggg gct gcc gag ccg gga ccc ccg cgc acc ccg cgc ccc ggg      257
Gly Ala Gly Ala Ala Glu Pro Gly Pro Pro Arg Thr Pro Arg Pro Gly
         45                  50                  55 cgg cgc gag ccg gtc atg ccg cgg ccg ccg gtg ccg gcg aac gcg ctg      305
Arg Arg Glu Pro Val Met Pro Arg Pro Pro Val Pro Ala Asn Ala Leu
 60                  65                  70                  75 ggc gcg cgg ggc gag gcg gtg cgg ctg cag ctg cag ggc gag gag ctg      353
Gly Ala Arg Gly Glu Ala Val Arg Leu Gln Leu Gln Gly Glu Glu Leu
             80                  85                  90 cgg ctg cag gag gag agc gtg cgg ctg cac cag att aac atc tac ctc      401
Arg Leu Gln Glu Glu Ser Val Arg Leu His Gln Ile Asn Ile Tyr Leu
         95                 100                 105 agc gac cgc atc tca ctg cac cgc cgc ctg ccc gag cgc tgg aac ccg      449
Ser Asp Arg Ile Ser Leu His Arg Arg Leu Pro Glu Arg Trp Asn Pro
        110                 115                 120 ctg tgc aaa gag aag aaa tat gat tat gat aat ttg ccc agg aca tct      497
Leu Cys Lys Glu Lys Lys Tyr Asp Tyr Asp Asn Leu Pro Arg Thr Ser
    125                 130                 135 gtt atc ata gca ttt tat aat gaa gcc tgg tca act ctc ctt cgg aca      545
Val Ile Ile Ala Phe Tyr Asn Glu Ala Trp Ser Thr Leu Leu Arg Thr
140                 145                 150                 155 gtt tac agt gtc ctt gag aca tcc ccg gat atc ctg cta gaa gaa gtg      593
Val Tyr Ser Val Leu Glu Thr Ser Pro Asp Ile Leu Leu Glu Glu Val
                160                 165                 170 atc ctt gta gat gac tac agt gat aga gag cac ctg aag gag cgc ttg      641
Ile Leu Val Asp Asp Tyr Ser Asp Arg Glu His Leu Lys Glu Arg Leu
            175                 180                 185 gcc aat gag ctt tcg gga ctg ccc aag gtg cgc ctg atc cgc gcc aac      689
Ala Asn Glu Leu Ser Gly Leu Pro Lys Val Arg Leu Ile Arg Ala Asn
        190                 195                 200 aag aga gag ggc ctg gtg cga gcc cgg ctg ctg ggg gcg tct gcg gcg      737
Lys Arg Glu Gly Leu Val Arg Ala Arg Leu Leu Gly Ala Ser Ala Ala
    205                 210                 215 agg ggc gat gtt ctg acc ttc ctg gac tgt cac tgt gag tgc cac gaa      785
Arg Gly Asp Val Leu Thr Phe Leu Asp Cys His Cys Glu Cys His Glu
220                 225                 230                 235 ggg tgg ctg gag ccg ctg ctg cag agg atc cat gaa gag gag tcg gca      833
Gly Trp Leu Glu Pro Leu Leu Gln Arg Ile His Glu Glu Glu Ser Ala
                240                 245                 250 gtg gtg tgc ccg gtg att gat gtg atc gac tgg aac acc ttc gaa tac      881
Val Val Cys Pro Val Ile Asp Val Ile Asp Trp Asn Thr Phe Glu Tyr
            255                 260                 265 ctg ggg aac tcc ggg gag ccc cag atc ggc ggt ttc gac tgg agg ctg      929
Leu Gly Asn Ser Gly Glu Pro Gln Ile Gly Gly Phe Asp Trp Arg Leu
        270                 275                 280 gtg ttc acg tgg cac aca gtt cct gag agg gag agg ata cgg atg caa      977
Val Phe Thr Trp His Thr Val Pro Glu Arg Glu Arg Ile Arg Met Gln
    285                 290                 295 tcc ccc gtc gat gtc atc agg tct cca aca atg gct ggt ggg ctg ttt     1025
Ser Pro Val Asp Val Ile Arg Ser Pro Thr Met Ala Gly Gly Leu Phe
300                 305                 310                 315 gct gtg agt aag aaa tat ttt gaa tat ctg ggg tct tat gat aca gga     1073
Ala Val Ser Lys Lys Tyr Phe Glu Tyr Leu Gly Ser Tyr Asp Thr Gly
```

-continued

```
                320                 325                 330
atg gaa gtt tgg gga gga gaa aac ctc gaa ttt tcc ttt agg atc tgg    1121
Met Glu Val Trp Gly Gly Glu Asn Leu Glu Phe Ser Phe Arg Ile Trp
                335                 340                 345 cag tgt ggt ggg gtt ctg gaa aca cac cca tgt tcc cat gtt ggc cat    1169
Gln Cys Gly Gly Val Leu Glu Thr His Pro Cys Ser His Val Gly His
        350                 355                 360 gtt ttc ccc aag caa gct ccc tac tcc cgc aac aag gct ctg gcc aac    1217
Val Phe Pro Lys Gln Ala Pro Tyr Ser Arg Asn Lys Ala Leu Ala Asn
365                 370                 375 agt gtt cgt gca gct gaa gta tgg atg gat gaa ttt aaa gag ctc tac    1265
Ser Val Arg Ala Ala Glu Val Trp Met Asp Glu Phe Lys Glu Leu Tyr
380                 385                 390                 395 tac cat cgc aac ccc cgt gcc cgc ttg gaa cct ttt ggg gat gtg aca    1313
Tyr His Arg Asn Pro Arg Ala Arg Leu Glu Pro Phe Gly Asp Val Thr
                400                 405                 410 gag agg aag cag ctc cgg gac aag ctc cag tgt aaa gac ttc aag tgg    1361
Glu Arg Lys Gln Leu Arg Asp Lys Leu Gln Cys Lys Asp Phe Lys Trp
            415                 420                 425 ttc ttg gag act gtg tat cca gaa ctg cat gtg cct gag gac agg cct    1409
Phe Leu Glu Thr Val Tyr Pro Glu Leu His Val Pro Glu Asp Arg Pro
        430                 435                 440 ggc ttc ttc ggg atg ctc cag aac aaa gga cta aca gac tac tgc ttt    1457
Gly Phe Phe Gly Met Leu Gln Asn Lys Gly Leu Thr Asp Tyr Cys Phe
    445                 450                 455 gac tat aac cct ccc gat gaa aac cag att gtg gga cac cag gtc att    1505
Asp Tyr Asn Pro Pro Asp Glu Asn Gln Ile Val Gly His Gln Val Ile
460                 465                 470                 475 ctg tac ctc tgt cat ggg atg ggc cag aat cag ttt ttc gag tac acg    1553
Leu Tyr Leu Cys His Gly Met Gly Gln Asn Gln Phe Phe Glu Tyr Thr
                480                 485                 490 tcc cag aaa gaa ata cgc tat aac acc cac cag cct gag ggc tgc att    1601
Ser Gln Lys Glu Ile Arg Tyr Asn Thr His Gln Pro Glu Gly Cys Ile
            495                 500                 505 gct gtg gaa gca gga atg gat acc ctt atc atg cat ctc tgc gaa gaa    1649
Ala Val Glu Ala Gly Met Asp Thr Leu Ile Met His Leu Cys Glu Glu
        510                 515                 520 act gcc cca gag aat cag aag ttc atc ttg cag gag gat gga tct tta    1697
Thr Ala Pro Glu Asn Gln Lys Phe Ile Leu Gln Glu Asp Gly Ser Leu
    525                 530                 535 ttt cac gaa cag tcc aag aaa tgt gtc cag gct gcg agg aag gag tcg    1745
Phe His Glu Gln Ser Lys Lys Cys Val Gln Ala Ala Arg Lys Glu Ser
540                 545                 550                 555 agt gac agt ttc gtt cca ctc tta cga gac tgc acc aac tcg gat cat    1793
Ser Asp Ser Phe Val Pro Leu Leu Arg Asp Cys Thr Asn Ser Asp His
                560                 565                 570 cag aaa tgg ttc ttc aaa gag cgc atg tta tga agcctcgtgt atcaaggagc    1846
Gln Lys Trp Phe Phe Lys Glu Arg Met Leu *
            575                 580 ccatcgaagg agactgtgga gccaggactc tgcccaacaa agacttagct aagcagtgac   1906
cagaacccac caaaaactag gctgcattgc tttgaagagg caatcatttt gccatttgtg   1966
aaagttgtgt tggatttagt aaaaatgtga ataagctttg tacttatttt gagaactttt   2026
taaatgttcc aaaataccct attttcaaag ggtaatcgta agatgttaac ccttggtatt   2086

tagaaaatta aaaccttata atatttttct aтcaaraWrW aWattttaca gtcgtgcctt   2146

ttactctcat tagcaaaaaa gataaagatt tattttggt atttacaaga attcccaggt   2206
acgaagatat ctgcatgggt ggaaatcagg ttcaagcaac gtactttgca ttaactgata   2266
```

-continued

| | |
|---|---|
| atacctcagc tgcggggtta aagttttccc agtatagaga gactgtcact aggaacattg | 2326 |
| tattgattta ttcaggtcat tgagatcttc tagatgtatt ttaaaaagaa tgctttttgg | 2386 |
| ttatgtgttg ctaccacagt taacactcca taatgttcat gtcagccaaa gaggactaac | 2446 |
| caaagctgaa atctcagaga acaatttgct ttactaagct gagtcaactt gagagcgaac | 2506 |
| ttctaacaat gccgcactgt agtgtggctg gttctaccac tatgacttta aaacatgttt | 2566 |
| atatcatttt taatttttat gatacggtag tgtcagggag aaatgtaatg ttctatatga | 2626 |
| aattccttt tcaagtttgt tcattaataa cagttattaa tttaaatcag cgttagagtt | 2686 |
| tgtgctgctg caactgctgt gaaaatttct ctgagtaatt ctgatttgtg aatgatccca | 2746 |
| gaccaaccct gagattttgt caacctgatt aagtcaatat gaatgattaa aaagatgtga | 2806 |
| gaacaaaaaa aaaaaaaaaa aaaaaaaaaa aaaaaaaaaa aaaa | 2850 |

<210> SEQ ID NO 2
<211> LENGTH: 581
<212> TYPE: PRT
<213> ORGANISM: homo sapiens

<400> SEQUENCE: 2

Met Trp Gly Arg Thr Ala Arg Arg Cys Pro Arg Glu Leu Arg Arg
1               5                   10                  15

Gly Arg Glu Ala Leu Val Leu Leu Ala Leu Leu Ala Leu Ala Gly
            20                  25                  30

Leu Gly Ser Val Leu Arg Ala Gln Arg Gly Ala Gly Ala Ala
        35                  40                  45

Glu Pro Gly Pro Pro Arg Thr Pro Arg Pro Gly Arg Arg Glu Pro Val
50                  55                  60

Met Pro Arg Pro Pro Val Pro Ala Asn Ala Leu Gly Ala Arg Gly Glu
65                  70                  75                  80

Ala Val Arg Leu Gln Leu Gln Gly Glu Glu Leu Arg Leu Gln Glu Glu
            85                  90                  95

Ser Val Arg Leu His Gln Ile Asn Ile Tyr Leu Ser Asp Arg Ile Ser
            100                 105                 110

Leu His Arg Arg Leu Pro Glu Arg Trp Asn Pro Leu Cys Lys Glu Lys
        115                 120                 125

Lys Tyr Asp Tyr Asp Asn Leu Pro Arg Thr Ser Val Ile Ile Ala Phe
130                 135                 140

Tyr Asn Glu Ala Trp Ser Thr Leu Leu Arg Thr Val Tyr Ser Val Leu
145                 150                 155                 160

Glu Thr Ser Pro Asp Ile Leu Leu Glu Glu Val Ile Leu Val Asp Asp
                165                 170                 175

Tyr Ser Asp Arg Glu His Leu Lys Glu Arg Leu Ala Asn Glu Leu Ser
            180                 185                 190

Gly Leu Pro Lys Val Arg Leu Ile Arg Ala Asn Lys Arg Glu Gly Leu
        195                 200                 205

Val Arg Ala Arg Leu Leu Gly Ala Ser Ala Ala Arg Gly Asp Val Leu
    210                 215                 220

Thr Phe Leu Asp Cys His Cys Glu Cys His Glu Gly Trp Leu Glu Pro
225                 230                 235                 240

Leu Leu Gln Arg Ile His Glu Glu Ser Ala Val Val Cys Pro Val
            245                 250                 255

Ile Asp Val Ile Asp Trp Asn Thr Phe Glu Tyr Leu Gly Asn Ser Gly
            260                 265                 270

```
Glu Pro Gln Ile Gly Gly Phe Asp Trp Arg Leu Val Phe Thr Trp His
            275                 280                 285
Thr Val Pro Glu Arg Glu Arg Ile Arg Met Gln Ser Pro Val Asp Val
        290                 295                 300
Ile Arg Ser Pro Thr Met Ala Gly Gly Leu Phe Ala Val Ser Lys Lys
305                 310                 315                 320
Tyr Phe Glu Tyr Leu Gly Ser Tyr Asp Thr Gly Met Glu Val Trp Gly
                325                 330                 335
Gly Glu Asn Leu Glu Phe Ser Phe Arg Ile Trp Gln Cys Gly Gly Val
            340                 345                 350
Leu Glu Thr His Pro Cys Ser His Val Gly His Val Phe Pro Lys Gln
        355                 360                 365
Ala Pro Tyr Ser Arg Asn Lys Ala Leu Ala Asn Ser Val Arg Ala Ala
    370                 375                 380
Glu Val Trp Met Asp Glu Phe Lys Glu Leu Tyr Tyr His Arg Asn Pro
385                 390                 395                 400
Arg Ala Arg Leu Glu Pro Phe Gly Asp Val Thr Glu Arg Lys Gln Leu
                405                 410                 415
Arg Asp Lys Leu Gln Cys Lys Asp Phe Lys Trp Phe Leu Glu Thr Val
            420                 425                 430
Tyr Pro Glu Leu His Val Pro Glu Asp Arg Pro Gly Phe Phe Gly Met
        435                 440                 445
Leu Gln Asn Lys Gly Leu Thr Asp Tyr Cys Phe Asp Tyr Asn Pro Pro
    450                 455                 460
Asp Glu Asn Gln Ile Val Gly His Gln Val Ile Leu Tyr Leu Cys His
465                 470                 475                 480
Gly Met Gly Gln Asn Gln Phe Phe Glu Tyr Thr Ser Gln Lys Glu Ile
                485                 490                 495
Arg Tyr Asn Thr His Gln Pro Glu Gly Cys Ile Ala Val Glu Ala Gly
            500                 505                 510
Met Asp Thr Leu Ile Met His Leu Cys Glu Glu Thr Ala Pro Glu Asn
        515                 520                 525
Gln Lys Phe Ile Leu Gln Glu Asp Gly Ser Leu Phe His Glu Gln Ser
    530                 535                 540
Lys Lys Cys Val Gln Ala Ala Arg Lys Glu Ser Ser Asp Ser Phe Val
545                 550                 555                 560
Pro Leu Leu Arg Asp Cys Thr Asn Ser Asp His Gln Lys Trp Phe Phe
                565                 570                 575
Lys Glu Arg Met Leu
            580

<210> SEQ ID NO 3
<211> LENGTH: 1746
<212> TYPE: DNA
<213> ORGANISM: homo sapiens
<220> FEATURE:
<221> NAME/KEY: CDS
<222> LOCATION: (1)...(1746)

<400> SEQUENCE: 3 atg tgg ggg cgc acg gcg cgg cgg cgc tgc ccg cgg gaa ctg cgg cgc        48
Met Trp Gly Arg Thr Ala Arg Arg Arg Cys Pro Arg Glu Leu Arg Arg
 1               5                  10                  15 ggc cgg gag gcg ctg ttg gtg ctc ctg gcg cta ctg gcg ttg gcc ggg        96
Gly Arg Glu Ala Leu Leu Val Leu Leu Ala Leu Leu Ala Leu Ala Gly
            20                  25                  30
```

-continued

| | |
|---|---|
| ctg ggc tcg gtg ctg cgg gcg cag cgt ggg gcc ggg gcc ggg gct gcc<br>Leu Gly Ser Val Leu Arg Ala Gln Arg Gly Ala Gly Ala Gly Ala Ala<br>35 40 45 | 144 |
| gag ccg gga ccc ccg cgc acc ccg cgc ccc ggg cgg cgc gag ccg gtc<br>Glu Pro Gly Pro Pro Arg Thr Pro Arg Pro Gly Arg Arg Glu Pro Val<br>50 55 60 | 192 |
| atg ccg cgg ccg ccg gtg ccg gcg aac gcg ctg ggc gcg cgg ggc gag<br>Met Pro Arg Pro Pro Val Pro Ala Asn Ala Leu Gly Ala Arg Gly Glu<br>65 70 75 80 | 240 |
| gcg gtg cgg ctg cag ctg cag ggc gag gag ctg cgg ctg cag gag gag<br>Ala Val Arg Leu Gln Leu Gln Gly Glu Glu Leu Arg Leu Gln Glu Glu<br>85 90 95 | 288 |
| agc gtg cgg ctg cac cag att aac atc tac ctc agc gac cgc atc tca<br>Ser Val Arg Leu His Gln Ile Asn Ile Tyr Leu Ser Asp Arg Ile Ser<br>100 105 110 | 336 |
| ctg cac cgc cgc ctg ccc gag cgc tgg aac ccg ctg tgc aaa gag aag<br>Leu His Arg Arg Leu Pro Glu Arg Trp Asn Pro Leu Cys Lys Glu Lys<br>115 120 125 | 384 |
| aaa tat gat tat gat aat ttg ccc agg aca tct gtt atc ata gca ttt<br>Lys Tyr Asp Tyr Asp Asn Leu Pro Arg Thr Ser Val Ile Ile Ala Phe<br>130 135 140 | 432 |
| tat aat gaa gcc tgg tca act ctc ctt cgg aca gtt tac agt gtc ctt<br>Tyr Asn Glu Ala Trp Ser Thr Leu Leu Arg Thr Val Tyr Ser Val Leu<br>145 150 155 160 | 480 |
| gag aca tcc ccg gat atc ctg cta gaa gaa gtg atc ctt gta gat gac<br>Glu Thr Ser Pro Asp Ile Leu Leu Glu Glu Val Ile Leu Val Asp Asp<br>165 170 175 | 528 |
| tac agt gat aga gag cac ctg aag gag cgc ttg gcc aat gag ctt tcg<br>Tyr Ser Asp Arg Glu His Leu Lys Glu Arg Leu Ala Asn Glu Leu Ser<br>180 185 190 | 576 |
| gga ctg ccc aag gtg cgc ctg atc cgc gcc aac aag aga gag ggc ctg<br>Gly Leu Pro Lys Val Arg Leu Ile Arg Ala Asn Lys Arg Glu Gly Leu<br>195 200 205 | 624 |
| gtg cga gcc cgg ctg ctg ggg gcg tct gcg gcg agg ggc gat gtt ctg<br>Val Arg Ala Arg Leu Leu Gly Ala Ser Ala Ala Arg Gly Asp Val Leu<br>210 215 220 | 672 |
| acc ttc ctg gac tgt cac tgt gag tgc cac gaa ggg tgg ctg gag ccg<br>Thr Phe Leu Asp Cys His Cys Glu Cys His Glu Gly Trp Leu Glu Pro<br>225 230 235 240 | 720 |
| ctg ctg cag agg atc cat gaa gag gag tcg gca gtg gtg tgc ccg gtg<br>Leu Leu Gln Arg Ile His Glu Glu Glu Ser Ala Val Val Cys Pro Val<br>245 250 255 | 768 |
| att gat gtg atc gac tgg aac acc ttc gaa tac ctg ggg aac tcc ggg<br>Ile Asp Val Ile Asp Trp Asn Thr Phe Glu Tyr Leu Gly Asn Ser Gly<br>260 265 270 | 816 |
| gag ccc cag atc ggc ggt ttc gac tgg agg ctg gtg ttc acg tgg cac<br>Glu Pro Gln Ile Gly Gly Phe Asp Trp Arg Leu Val Phe Thr Trp His<br>275 280 285 | 864 |
| aca gtt cct gag agg gag agg ata cgg atg caa tcc ccc gtc gat gtc<br>Thr Val Pro Glu Arg Glu Arg Ile Arg Met Gln Ser Pro Val Asp Val<br>290 295 300 | 912 |
| atc agg tct cca aca atg gct ggt ggg ctg ttt gct gtg agt aag aaa<br>Ile Arg Ser Pro Thr Met Ala Gly Gly Leu Phe Ala Val Ser Lys Lys<br>305 310 315 320 | 960 |
| tat ttt gaa tat ctg ggg tct tat gat aca gga atg gaa gtt tgg gga<br>Tyr Phe Glu Tyr Leu Gly Ser Tyr Asp Thr Gly Met Glu Val Trp Gly<br>325 330 335 | 1008 |
| gga gaa aac ctc gaa ttt tcc ttt agg atc tgg cag tgt ggt ggg gtt<br>Gly Glu Asn Leu Glu Phe Ser Phe Arg Ile Trp Gln Cys Gly Gly Val | 1056 |

```
ctg gaa aca cac cca tgt tcc cat gtt ggc cat gtt ttc ccc aag caa      1104
Leu Glu Thr His Pro Cys Ser His Val Gly His Val Phe Pro Lys Gln
            355                 360                 365 gct ccc tac tcc cgc aac aag gct ctg gcc aac agt gtt cgt gca gct      1152
Ala Pro Tyr Ser Arg Asn Lys Ala Leu Ala Asn Ser Val Arg Ala Ala
    370                 375                 380 gaa gta tgg atg gat gaa ttt aaa gag ctc tac tac cat cgc aac ccc      1200
Glu Val Trp Met Asp Glu Phe Lys Glu Leu Tyr Tyr His Arg Asn Pro
385                 390                 395                 400 cgt gcc cgc ttg gaa cct ttt ggg gat gtg aca gag agg aag cag ctc      1248
Arg Ala Arg Leu Glu Pro Phe Gly Asp Val Thr Glu Arg Lys Gln Leu
                405                 410                 415 cgg gac aag ctc cag tgt aaa gac ttc aag tgg ttc ttg gag act gtg      1296
Arg Asp Lys Leu Gln Cys Lys Asp Phe Lys Trp Phe Leu Glu Thr Val
            420                 425                 430 tat cca gaa ctg cat gtg cct gag gac agg cct ggc ttc ttc ggg atg      1344
Tyr Pro Glu Leu His Val Pro Glu Asp Arg Pro Gly Phe Phe Gly Met
        435                 440                 445 ctc cag aac aaa gga cta aca gac tac tgc ttt gac tat aac cct ccc      1392
Leu Gln Asn Lys Gly Leu Thr Asp Tyr Cys Phe Asp Tyr Asn Pro Pro
    450                 455                 460 gat gaa aac cag att gtg gga cac cag gtc att ctg tac ctc tgt cat      1440
Asp Glu Asn Gln Ile Val Gly His Gln Val Ile Leu Tyr Leu Cys His
465                 470                 475                 480 ggg atg ggc cag aat cag ttt ttc gag tac acg tcc cag aaa gaa ata      1488
Gly Met Gly Gln Asn Gln Phe Phe Glu Tyr Thr Ser Gln Lys Glu Ile
                485                 490                 495 cgc tat aac acc cac cag cct gag ggc tgc att gct gtg gaa gca gga      1536
Arg Tyr Asn Thr His Gln Pro Glu Gly Cys Ile Ala Val Glu Ala Gly
            500                 505                 510 atg gat acc ctt atc atg cat ctc tgc gaa gaa act gcc cca gag aat      1584
Met Asp Thr Leu Ile Met His Leu Cys Glu Glu Thr Ala Pro Glu Asn
        515                 520                 525 cag aag ttc atc ttg cag gag gat gga tct tta ttt cac gaa cag tcc      1632
Gln Lys Phe Ile Leu Gln Glu Asp Gly Ser Leu Phe His Glu Gln Ser
    530                 535                 540 aag aaa tgt gtc cag gct gcg agg aag gag tcg agt gac agt ttc gtt      1680
Lys Lys Cys Val Gln Ala Ala Arg Lys Glu Ser Ser Asp Ser Phe Val
545                 550                 555                 560 cca ctc tta cga gac tgc acc aac tcg gat cat cag aaa tgg ttc ttc      1728
Pro Leu Leu Arg Asp Cys Thr Asn Ser Asp His Gln Lys Trp Phe Phe
                565                 570                 575 aaa gag cgc atg tta tga                                              1746
Lys Glu Arg Met Leu *
            580
```

<210> SEQ ID NO 4
<211> LENGTH: 187
<212> TYPE: PRT
<213> ORGANISM: Artificial Sequence
<220> FEATURE:
<223> OTHER INFORMATION: consensus

<400> SEQUENCE: 4

```
Ser Ile Val Ile Pro Thr Tyr Asn Glu Glu Ala Asp Tyr Leu Glu Glu
 1               5                  10                  15

Leu Leu Glu Ser Val Leu Ala Gln Ser Thr Leu Glu Asp Ile Glu Ile
             20                  25                  30

Ile Val Val Asp Asp Gly Ser Glu Thr Asp Glu Thr Val Glu Ile Ala
```

```
                35                   40                  45
Glu Asp Tyr Leu Asp Glu Arg Ile Lys Glu Glu Asn Pro Arg Ile Ile
         50                  55                  60

Ile Val Ile Arg Leu Glu Glu Asn Ser Gln Gly Pro Ala Ala Ala Arg
 65                  70                  75                  80

Asn Lys Gly Ile Arg Arg Ala Thr Gly Asp Ser Asp Tyr Ile Leu Phe
                 85                  90                  95

Leu Asp Ala Asp Asp Ile Phe Thr Pro Asp Lys Leu Glu Lys Leu Ile
            100                 105                 110

Asp Tyr Ala Glu Ala Thr Asp Ala Ala Val Val Leu Gly Ala Ile Asp
            115                 120                 125

Ala Tyr Glu Tyr Ala Glu Gly Glu Ser Asn Leu Tyr Arg Ile Ala Arg
            130                 135                 140

Ala Asp Thr Glu Arg Ser Leu Phe Ala Gly Leu Leu Arg Lys Thr Gly
145                 150                 155                 160

Arg Leu Thr Gly Gly Leu Glu Leu Ser Phe Glu Ile Gly Ser Asn Ala
                165                 170                 175

Ile Tyr Arg Arg Glu Ala Phe Glu Glu Leu Phe
            180                 185

<210> SEQ ID NO 5
<211> LENGTH: 145
<212> TYPE: PRT
<213> ORGANISM: Artificial Sequence
<220> FEATURE:
<223> OTHER INFORMATION: consensus

<400> SEQUENCE: 5

Arg Ser Val Phe Val Ile Thr Ile Leu Val Asn Gly Asn Ser Gly Arg
  1               5                  10                  15

Cys Leu Asp Val Asn Ser Ser Glu Ser Asp Gly Asn Gln Val Gln
             20                  25                  30

Leu Trp Asn Cys His Ser Asn Pro Gly Lys Asn Gln Lys Trp Ser Leu
             35                  40                  45

Thr Tyr Asp Glu Ser Asp Gly Glu Ile Arg Ser Val Val Asn Asn Asp
         50                  55                  60

Lys Cys Leu Thr Val Asn Ala Asn Ser Pro Gly Ser Glu Val Lys Leu
 65                  70                  75                  80

Tyr Gln Cys Asp Ser Ala Thr Ser Asp Asn Gln Lys Trp Glu Leu Asn
                 85                  90                  95

Asn Asp Gly Leu Ile Gly Asn Lys Ile Leu Asn Leu Val Asn Thr
            100                 105                 110

Gly Leu Val Leu Asp Val Lys Gly Ser Asp Thr Gln Asn Gly Thr Lys
            115                 120                 125

Leu Ile Leu Tyr Thr Cys Ser Gly Gly Arg Asn Gln Gln Trp Leu Pro
            130                 135                 140

Thr
145

<210> SEQ ID NO 6
<211> LENGTH: 135
<212> TYPE: PRT
<213> ORGANISM: Artificial Sequence
<220> FEATURE:
<223> OTHER INFORMATION: consensus

<400> SEQUENCE: 6
```

Arg Gly Tyr Phe Leu Ile Ile Gly Asn Thr Gly Leu Cys Leu Asp
1               5                   10                  15

Val Asn Gly Asn Ser Glu Ser Lys Ser Asp Gly Asn Pro Val Gln Leu
            20                  25                  30

Trp Asp Cys His Gly Gly Asn Gln Leu Trp Lys Leu Thr Tyr Asn
            35                  40                  45

Glu Ser Asp Gly Ala Ile Arg Ile Asn Ser Asp Leu Cys Leu Thr Val
    50                  55                  60

Asn Gly Thr Val Thr Leu Tyr Ser Cys Asp Gly Thr Asp Lys Gly Asn
65                      70                  75                  80

Asp Asn Gln Lys Trp Glu Val Asn Lys Asp Gly Thr Ile Arg Asn Pro
                85                  90                  95

Lys Asn Ser Lys Lys Gly Val Asp Ser Gly Leu Cys Leu Asp Val Lys
            100                 105                 110

Asp Gly Asn Lys Val Gln Leu Trp Thr Cys Asn Gly Ser Asp Ala Pro
            115                 120                 125

Asn Gln Lys Trp Ile Phe Glu
            130             135

<210> SEQ ID NO 7
<211> LENGTH: 166
<212> TYPE: PRT
<213> ORGANISM: Artificial Sequence
<220> FEATURE:
<223> OTHER INFORMATION: consensus

<400> SEQUENCE: 7

Trp His Tyr Val Pro Glu Glu Arg Lys Arg Arg Lys Asp Pro
1               5                   10                  15

Thr Asp Pro Ile Arg Ser Pro Thr Met Ala Gly Gly Leu Phe Ala Ile
            20                  25                  30

Asn Lys Glu Tyr Phe Glu Glu Leu Gly Thr Tyr Asp Pro Gly Met Asp
            35                  40                  45

Ile Trp Gly Gly Glu Asn Leu Glu Leu Ser Phe Arg Val Trp Gln Cys
    50                  55                  60

Gly Gly Arg Leu Glu Ile Val Pro Cys Ser His Val Gly His Val Phe
65                      70                  75                  80

Arg Lys Arg Ser Pro Tyr Thr Phe Pro Gly Lys Gly Ser Gly Lys Asp
                85                  90                  95

Val Ile Ser Arg Asn Thr Val Arg Val Ala Glu Val Trp Met Asp Asp
            100                 105                 110

Tyr Lys Glu Tyr Phe Tyr Lys His Asn Pro Gln Ala Arg Lys Val Arg
            115                 120                 125

Asp Phe Gly Asp Ile Ser Glu Arg Lys Glu Leu Arg Glu Lys Leu Gln
            130                 135                 140

Cys Lys Ser Phe Lys Trp Tyr Leu Glu Asn Val Tyr Pro Asp Leu Tyr
145                 150                 155                 160

Val Pro Ala His Glu Pro
                165

<210> SEQ ID NO 8
<211> LENGTH: 578
<212> TYPE: PRT
<213> ORGANISM: Mus musculus

<400> SEQUENCE: 8

Met Ala Val Arg Trp Thr Trp Ala Gly Lys Ser Cys Leu Leu Leu Ala

-continued

```
  1               5                    10                   15
Leu Leu Thr Leu Ala Tyr Ile Leu Val Glu Phe Ser Val Ser Thr Leu
             20                  25                  30

Tyr Ala Ser Pro Gly Ala Gly Gly Ala Arg Glu Leu Gly Pro Arg Arg
             35                  40                  45

Leu Pro Asp Leu Asp Thr Arg Glu Glu Asp Leu Ser Gln Pro Leu Tyr
 50                  55                  60

Ile Lys Pro Pro Ala Asp Ser His Ala Leu Gly Glu Trp Gly Arg Ala
 65                  70                  75                  80

Ser Lys Leu Gln Leu Asn Glu Gly Glu Leu Lys Gln Gln Glu Glu Leu
                 85                  90                  95

Ile Glu Arg Tyr Ala Ile Asn Ile Tyr Leu Ser Asp Arg Ile Ser Leu
                100                 105                 110

His Arg His Ile Glu Asp Lys Arg Met Tyr Glu Cys Lys Ala Lys Lys
            115                 120                 125

Phe His Tyr Arg Ser Leu Pro Thr Thr Ser Val Ile Ile Ala Phe Tyr
        130                 135                 140

Asn Glu Ala Trp Ser Thr Leu Leu Arg Thr Ile His Ser Val Leu Glu
145                 150                 155                 160

Thr Ser Pro Ala Val Leu Leu Lys Glu Ile Ile Leu Val Asp Asp Leu
                165                 170                 175

Ser Asp Arg Ile Tyr Leu Lys Ala Gln Leu Glu Thr Tyr Ile Ser Asn
            180                 185                 190

Leu Glu Arg Val Arg Leu Ile Arg Thr Asn Lys Arg Glu Gly Leu Val
        195                 200                 205

Arg Ala Arg Leu Ile Gly Ala Thr Phe Ala Thr Gly Asp Val Leu Thr
210                 215                 220

Phe Leu Asp Cys His Cys Glu Cys Asn Thr Gly Trp Leu Glu Pro Leu
225                 230                 235                 240

Leu Glu Arg Ile Ser Arg Asp Glu Thr Ala Ile Val Cys Pro Val Ile
                245                 250                 255

Asp Thr Ile Asp Trp Asn Thr Phe Glu Phe Tyr Met Gln Thr Gly Glu
            260                 265                 270

Pro Met Ile Gly Gly Phe Asp Trp Arg Leu Thr Phe Gln Trp His Ser
        275                 280                 285

Val Pro Lys His Glu Arg Asp Arg Arg Thr Ser Arg Ile Asp Pro Ile
    290                 295                 300

Arg Ser Pro Thr Met Ala Gly Gly Leu Phe Ala Val Ser Lys Lys Tyr
305                 310                 315                 320

Phe Gln Tyr Leu Gly Thr Tyr Asp Thr Gly Met Glu Val Trp Gly Gly
                325                 330                 335

Glu Asn Leu Glu Leu Ser Phe Arg Val Trp Gln Cys Gly Gly Lys Leu
            340                 345                 350

Glu Ile His Pro Cys Ser His Val Gly His Val Phe Pro Lys Arg Ala
        355                 360                 365

Pro Tyr Ala Arg Pro Asn Phe Leu Gln Asn Thr Ala Arg Ala Ala Glu
    370                 375                 380

Val Trp Met Asp Glu Tyr Lys Glu His Phe Tyr Asn Arg Asn Pro Pro
385                 390                 395                 400

Ala Arg Lys Glu Ala Tyr Gly Asp Leu Ser Glu Arg Lys Leu Leu Arg
                405                 410                 415

Glu Arg Leu Lys Cys Lys Ser Phe Asp Trp Tyr Leu Lys Asn Val Phe
            420                 425                 430
```

```
Ser Asn Leu His Val Pro Glu Asp Arg Pro Gly Trp His Gly Ala Ile
        435             440                 445

Arg Ser Met Gly Ile Ser Ser Glu Cys Leu Asp Tyr Asn Ala Pro Asp
    450             455                 460

Asn Asn Pro Thr Gly Ala Asn Leu Ser Leu Phe Gly Cys His Gly Gln
465             470                 475                 480

Gly Gly Asn Gln Phe Phe Glu Tyr Thr Ser Asn Lys Glu Ile Arg Phe
                485                 490                 495

Asn Ser Val Thr Glu Leu Cys Ala Glu Val Pro Gln Gln Lys Asp Tyr
            500                 505                 510

Val Gly Met Gln Asn Cys Pro Lys Asp Gly Leu Pro Val Pro Val Asn
        515                 520                 525

Ile Ile Trp His Phe Lys Glu Asp Gly Thr Ile Phe His Pro His Thr
    530                 535                 540

Arg Leu Cys Leu Ser Ala Tyr Arg Thr Ala Glu Gly Arg Pro Ser Val
545             550                 555                 560

His Met Lys Thr Cys Asp Ala Leu Asp Lys Asn Gln Leu Trp Arg Phe
                565                 570                 575

Glu Lys

<210> SEQ ID NO 9
<211> LENGTH: 22
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)...(22)
<223> OTHER INFORMATION: Xaa = any amino acid

<400> SEQUENCE: 9

Leu Xaa Xaa Xaa Xaa Xaa Xaa Leu Xaa Xaa Xaa Xaa Xaa Xaa Leu Xaa
1               5                   10                  15

Xaa Xaa Xaa Xaa Xaa Leu
            20
```

33945, A HUMAN GLYCOSYLTRANSFERASE FAMILY MEMBER AND USES THEREFOR

CROSS-REFERENCES TO RELATED APPLICATIONS

This application claims the benefit of U.S. Provisional Application No. 60/269,202, filed Feb. 15, 2001, the contents of which are incorporated herein by this reference.

BACKGROUND OF THE INVENTION

A great diversity of oligosaccharide structures and types of glycoconjugates is found in nature, and these are synthesized by a large number of glycosyltransferases. Glycosyltransferases catalyze the synthesis of glycoconjugates, including glycolipids, glycoproteins, and polysaccharides, by transferring an activated mono- or oligosaccharide residue to an existing acceptor molecule for the initiation or elongation of the carbohydrate chain. A catalytic reaction is believed to involve the recognition of both the donor and acceptor by suitable domains, as well as the catalytic site of the enzyme (Amado et al. (1999) *Biochim Biophys Acta* 1473:35–53; Kapitonov et al. (1999) *Glycobiology* 9:961–78).

Because the glycosylation reaction is highly specific with respect to both the configuration of the sugar residue and the site of the addition, it is expected that unique domain structures for substrate recognition and nucleotide-sugar binding are located within the enzyme molecule. Evidence indicates that formation of many glycosidic linkages is covered by large homologous glycosyltransferase gene families, and that the existence of multiple enzyme isoforms provides a degree of redundancy as well as a higher level of regulation of the glycoforms synthesized (Kapitonov et al. (1999) *Glycobiology* 9:961–78).

Glycosylation is the principal chemical modification to proteins as they pass through Golgi vesicles. Thus, some glycosyltransferases reside in Golgi membranes. Other glycosyltransferases reside in the endoplasmic reticulum membrane. Some glycosyltransferases are present on the cell surface and are thought to function as cell adhesion molecules by binding oligosaccharide substrates on adjacent cell surfaces or in the extracellular matrix. The best studied of these is beta 1,4-galactosyltransferase, which mediates sperm binding to the egg coat and selected cell interactions with the basal lamina (Shur (1993) *Curr Opin Cell Biol* 5:854–63).

SUMMARY OF THE INVENTION

The present invention is based, in part, on the discovery of a novel glycosyltransferase family member, referred to herein as "33945". The nucleotide sequence of a cDNA encoding 33945 is shown in SEQ ID NO:1, and the amino acid sequence of a 33945 polypeptide is shown in SEQ ID NO:2. In addition, the nucleotide sequence of the coding region is depicted in SEQ ID NO:3.

Accordingly, in one aspect, the invention features a nucleic acid molecule which encodes a 33945 protein or polypeptide, e.g., a biologically active portion of the 33945 protein. In a preferred embodiment, the isolated nucleic acid molecule encodes a polypeptide having the amino acid sequence of SEQ ID NO:2. In other embodiments, the invention provides isolated 33945 nucleic acid molecules having the nucleotide sequence shown in SEQ ID NO:1 or SEQ ID NO:3. In still other embodiments, the invention provides nucleic acid molecules that are sufficiently or substantially identical (e.g., naturally occurring allelic variants) to the nucleotide sequence shown in SEQ ID NO:1 or SEQ ID NO:3. In other embodiments, the invention provides a nucleic acid molecule which hybridizes under stringent hybridization conditions to a nucleic acid molecule comprising the nucleotide sequence of SEQ ID NO:1 or SEQ ID NO:3, wherein the nucleic acid encodes a full length 33945 protein or an active fragment thereof.

In a related aspect, the invention further provides nucleic acid constructs which include a 33945 nucleic acid molecule described herein. In certain embodiments, the nucleic acid molecules of the invention are operatively linked to native or heterologous regulatory sequences. Also included are vectors and host cells containing the 33945 nucleic acid molecules of the invention e.g., vectors and host cells suitable for producing polypeptides.

In another related aspect, the invention provides nucleic acid fragments suitable as primers or hybridization probes for the detection of 33945-encoding nucleic acids.

In still another related aspect, isolated nucleic acid molecules that are antisense to a 33945 encoding nucleic acid molecule are provided.

In another aspect, the invention features 33945 polypeptides, and biologically active or antigenic fragments thereof that are useful, e.g., as reagents or targets in assays applicable to treatment and diagnosis of glycosyltransferase-associated or other 33945-associated, -mediated or -related disorders. In another embodiment, the invention provides 33945 polypeptides having a 33945 activity. Preferred polypeptides are 33945 proteins including at least one glycosyltransferase domain, and, preferably, having a 33945 activity, e.g., a 33945 activity as described herein.

In other embodiments, the invention provides 33945 polypeptides, e.g., a 33945 polypeptide having the amino acid sequence shown in SEQ ID NO:2 ; an amino acid sequence that is sufficiently or substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1 or SEQ ID NO:3, wherein the nucleic acid encodes a full length 33945 protein or an active fragment thereof.

In a related aspect, the invention further provides nucleic acid constructs which include a 33945 nucleic acid molecule described herein.

In a related aspect, the invention provides 33945 polypeptides or fragments operatively linked to non-33945 polypeptides to form fusion proteins.

In another aspect, the invention features antibodies and antigen-binding fragments thereof, that react with, or more preferably specifically or selectively bind 33945 polypeptides.

In another aspect, the invention provides methods of screening for compounds that modulate the expression or activity of the 33945 polypeptides or nucleic acids.

In still another aspect, the invention provides a process for modulating 33945 polypeptide or nucleic acid expression or activity, e.g., using the compounds identified in the screens described herein. In certain embodiments, the methods involve treatment of conditions or disorders involving aberrant or deficient glycosyltransferase function or expression. The treated conditions or disorders can involve aberrant or deficient protein glycosylation, or cellular adhesion.

Examples of such disorders, e.g., glycosyltransferase-associated disorders, include but are not limited to, cardiovascular disorders, e.g., atherosclerosis or endothelial cell disorders, pancreatic disorders, cellular proliferative and/or differentiative disorders, immune disorders, e.g., inflammatory disorders, viral diseases, and liver disorders.

The invention also provides assays for determining the activity of or the presence or absence of 33945 polypeptides or nucleic acid molecules in a biological sample, including for disease diagnosis.

In a further aspect, the invention provides assays for determining the presence or absence of a genetic alteration in a 33945 polypeptide or nucleic acid molecule, including for disease diagnosis.

Other features and advantages of the invention will be apparent from the following detailed description, and from the claims.

DETAILED DESCRIPTION OF THE INVENTION

Figure 1:
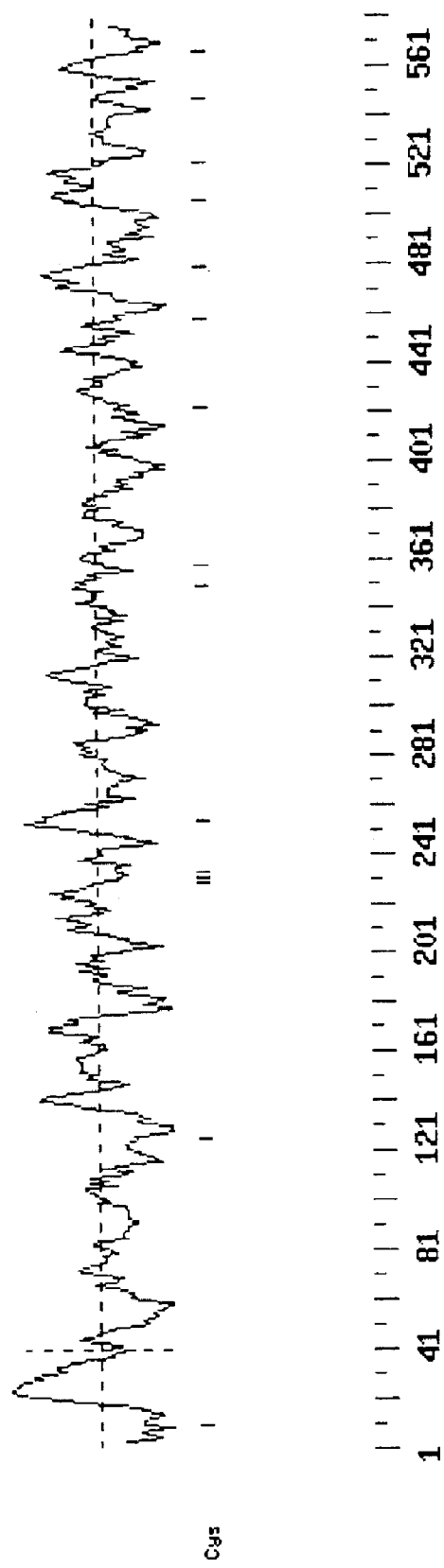
FIG. 1 depicts a hydropathy plot of human 33945. Relatively hydrophobic residues are shown above the dashed horizontal line, and relatively hydrophilic residues are below the dashed horizontal line. The cysteine residues (cys) are indicated by short vertical lines just below the hydropathy trace. The numbers corresponding to the amino acid sequence of human 33945 are indicated. Polypeptides of the invention include fragments which include: all or part of a hydrophobic sequence, e.g., a sequence above the dashed line, e.g., the sequence from about amino acid 20 to 29, from about 30 to 37, and from about 251 to 257 of SEQ ID NO:2; all or part of a hydrophilic sequence, e.g., a sequence below the dashed line, e.g., the sequence from about amino acid 126 to 134, from about 175 to 186, and from about 534 to 546 of SEQ ID NO:2; a sequence which includes a Cys, or a glycosylation site.

The human 33945 sequence (SEQ ID NO:1), which is approximately 2850 nucleotides long including untranslated regions, contains a predicted methionine-initiated coding sequence of about 1746 nucleotides, including the termination codon (nucleotides indicated as coding of SEQ ID NO:1; SEQ ID NO:3). The coding sequence encodes a 581 amino acid protein (SEQ ID NO:2).

Human 33945 contains the following regions or other structural features (for general information regarding PFAM identifiers, PS prefix and PF prefix domain identification numbers, refer to Sonnhammer et at. (1997) *Protein* 28:405–420 420 or the Pfam website maintained in several locations, e.g. by the Sanger Institute (pfam.sanger.ac.uk), Washington University (pfam.wustl.edu), the Karolinska Institute (pfam.car.kr.se) or Institut de la National Recherche Agronomique (pfam.iouy.inra.fr)):

a glycosyltransferase domain (group 2, PFAM Accession Number PF00535, SEQ ID NO:4) located at about amino acid residues 139 to 322 of SEQ ID NO:2;

a ricin beta-chain lectin domain (PFAM Accession Number PF00652, SEQ ID NO:5; SMART identifier: ricin, SEQ ID NO:6) located at about amino acid residues 441 to 577 of SEQ ID NO:2;

one transmembrane domain (predicted by MEMSAT, Jones et al. (1994) *Biochemistry* 33:3038–3049) at about amino acids 20 to 37 of SEQ ID NO:2;

one leucine zipper pattern (Prosite PS00029, SEQ ID NO:9) at about amino acids 86 to 107 of SEQ ID NO:2;

one RGD cell attachment sequence (Prosite PS00016) at about amino acids 220 to 222 of SEQ ID NO:2;

eleven Protein Kinase C phosphorylation sites (Prosite PS00005) at about amino acids 5 to 7, 55 to 57, 97 to 99, 108 to 110, 178 to 180, 318 to 320, 343 to 345, 380 to 382, 411 to 413, 492 to 494, and 544 to 546 of SEQ ID NO:2;

ten Casein Kinase II phosphorylation sites (Prosite PS00006) located at about amino acids 158 to 161, 162 to 165, 178 to 181, 225 to 228, 289 to 292, 300 to 303, 330 to 333, 492 to 495, 524 to 527, and 567 to 570 of SEQ ID NO:2;

one cAMP/cGMP-dependent protein kinase phosphorylation site (Prosite PS00004) located at about amino acids 552 to 555 of SEQ ID NO:2;

one tyrosine kinase phosphorylation site (Prosite PS00007) from about amino acids 426 to 433 of SEQ ID NO:2;

one amidation site (Prosite PS00009) from about amino acids 58 to 61 of SEQ ID NO:2; and eight N-myristoylation sites (Prosite PS00008) from about amino acids 42 to 47, 207 to 212, 215 to 220, 312 to 317, 326 to 331, 351 to 356,447 to 452, and 481 to 486 of SEQ ID NO:2.

The 33945 protein contains a significant number of structural characteristics in common with members of the glycosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologs of non-human origin, e.g., rat or mouse proteins. Members of a family can also have common functional characteristics.

As used herein, the term "glycosyltransferase" includes a protein or polypeptide which is capable of catalyzing the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate molecule. Glycosyltransferases can be divided into numerous subfamilies based upon their specificity for sugar moieties and acceptor molecules. Glycosyltransferases typically are integral membrane proteins; family members can be found, for example, in the Golgi apparatus, in the endoplasmic reticulum or in the cell membrane. The glycosyltransferase domain of human 33945 bears similarity to a subfamily designated "group 2" glycosyltransferases. These enzymes comprise a diverse subfamily, whose members transfer sugar from UDP-glucose, UDP-N-acetyl-galactosamine, GDP-mannose or CDP-abequose, to a range of substrates including cellulose, dolichol phosphate and teichoic acids.

Glycosyltransferases can have two types of topology. Glycosyltransferases of the Golgi do not possess an obvious sequence homology which would suggest a common Golgi retention signal. However, they are all membrane proteins and share type II topology. The Type II topology of glycosyltransferases (also shared by group 2 glycosyltransferases), consists essentially of an amino terminal cytoplasmic tail, a signal anchor transmembrane domain, a stem region, and a large luminal catalytic domain.

The membrane-spanning domain and its flanking regions contain necessary and sufficient information for Golgi retention of these enzymes (Jaskiewicz (1997) *Acta Biochim Pot* 44:173–9). Endoplasmic reticulum (ER) localized glycosyltransferases can have either a type II topology, like the Golgi glycosyltransferases, or a type I topology, e.g., the N-terminus and catalytic domain inside the ER (Kapitonov et al. (1999) *Glycobiology* 9:961–78). The 33945 protein is homologous to ProDom family PD003162 ("N-acetylgalactosaminyltransferas Transferase Polypeptide Acetylgalactosaminyltransferase UDP-GalNac:polypeptide Glycosyltransferase Protein-UDP-protein- UDP N-;" SEQ ID NO:7; ProDomain Release 2000.1; for ProDom information, refer to Institut National de la Recherche Agronomique (INRA)/Central National de la Recherche Scientifique (CNRA), Toulouse, France An alignment of 33945 with this consensus sequence shows 61% identity in the region at about amino acid residues 287 to 443 of SEQ ID NO:2. The 33945 protein shares 57.9% identity with mouse polypeptide GalNac transferase-T4, another glycosyltransferase (type 2) family member (Accession number 2121220 in GenPept, SEQ ID NO:8) as calculated from a matrix made by matblas from blosum62.iij.

A 33945 polypeptide can include a "glycosyltransferase domain" or regions homologous with a "glycosyltransferase domain".

As used herein, the term "glycosyltransferase domain" includes an amino acid sequence of about 100 to 250 amino acid residues in length and having a bit score for the alignment of the sequence to the glycosyltransferase domain (HMM) of at least 40. Preferably, a glycosyltransferase domain includes at least about 120 to 220 amino acids, more preferably about 140 to 200 amino acid residues, or about 160 to 190 amino acids and has a bit score for the alignment of the sequence to the glycosyltransferase domain (HMM) of at least 50, 60, 80 or greater. Preferably a glycosyltransferase domain mediates the transfer sugar from UDP-glucose, UDP-N-acetyl-galactosamine, GDP-mannose or CDP-abequose, to a range of substrates including cellulose, dolichol phosphate and teichoic acids. Glycosyltransferase domains (HMM) have been assigned numerous PFAM Accession Numbers, including PF00534 (group 1) and PF00535 (group 2) (see Pfam information at Washington University in St. Louis, Mo.). An alignment of the glycosyltransferase domain (amino acids 139 to 322 of SEQ ID NO:2) of human 33945 with a consensus amino acid sequence (group 2 glycosyltransferases, SEQ ID NO:4) derived from a hidden Markov model yields a bit score of 85.1.

In a preferred embodiment, a 33945 polypeptide or protein has a "glycosyltransferase domain" or a region which includes at least about 120 to 220 more preferably about 140 to 200 or 160 to 190 amino acid residues and has at least about 60%, 70% 80% 90% 95%, 99%, or 100% homology with a "glycosyltransferase domain," e.g., the glycosyltransferase domain of human 33945 (e.g., residues 139 to 322 of SEQ ID NO:2).

A 33945 polypeptide can further include a "ricin domain" or regions homologous with a "ricin domain," a transmembrane anchor and at least two nontransmembrane regions.

As used herein, the term "ricin domain" includes a protein or polypeptide which is capable of recognizing, e.g., binding, a sugar molecule and has an amino acid sequence of about 80 to 200 amino acid residues in length and having a bit score for the alignment of the sequence to the ricin domain based on SMART of at least 40 (see SMART information at European Molecular Biology Laboratory (EMBL), Heidelberg, Germany). Ricin domains are typically present in many carbohydrate binding proteins, e.g., plant and bacterial AB toxins, glycosidases and proteases. This domain, also known as the ricin B lectin domain, can be present in one or more copies and has been shown in some instances to bind to simple sugars, such as galactose and lactose. Preferably, a ricin domain includes at least about 100 to 180 amino acids, more preferably about 120 to 160 amino acid residues, or about 130 to 150 amino acids and has a bit score for the alignment of the sequence to the ricin domain (HMM) of at least 50, 60, 70 or greater. An alignment of the ricin domain (amino acids 441 to 577 of SEQ ID NO:2) of human 33945 with a consensus amino acid sequence (Ricin_B_lectin, Pfam) derived from a hidden Markov model yields a bit score of 18.7 and an alignment of the ricin domain (amino acids 445 to 577 of SEQ ID NO:2) of human 33945 with a consensus amino acid sequence (Ricin_3, SMART) derived from modular architecture analysis yields a bit score of 73.3.

In a preferred embodiment, the 33945 polypeptide or protein has a "ricin domain" or a region which includes at least about 100 to 180 more preferably about 120 to 160 or 130 to 150 amino acid residues and has at least about 70% 80% 90% 95%, 99%, or 100% homology with a "ricin domain," e.g., the ricin domain of human 33945 (e.g., residues 445 to 577 of SEQ ID NO:2).

To identify the presence of a "glycosyltransferase" domain or a "ricin" domain in a 33945 protein sequence, and make the determination that a polypeptide or protein of interest has a particular profile, the amino acid sequence of the protein can be searched against the Pfam database of HMMs (e.g., the Pfam database, release 2.1) using the default parameters see the Pfam website maintained in several locations, e.g. by the Sanger Institute (pfam.sanger.ac.uk/Software/Pfam/HMM search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) J. Mol. Biol. 235:1501–1531; and Stultz et al. (1993) *Protein Sci.* 2:305–314, the contents of which are incorporated herein by reference. A search was performed against the HMM database resulting in the identification of a "glycosyltransferase domain" domain in the amino acid sequence of human 33945 at about residues 139 to 322 of SEQ ID NO:2 and a "ricin domain" in the amino acid sequence of human 33945 at about residues 441 to 577 of SEQ ID NO:2.

The presence of a "ricin" domain in a 33945 protein sequence can also be identified using a SMART database (Simple Modular Architecture Research Tool, European Molecular Biology Laboratory (EMBL), Heidelberg, Germany of HMMs as described in Schultz et al. (1998), *Proc. Nat. Acad. Sci. USA* 95:5857 and Schultz et al. (2000) *Nucl. Acids Res* 28:231. The database contains domains identified by profiling with the hidden Markov models of the HMMer2 search program (R. Durbin et al. (1998) Biological sequence analysis: probabilistic models of proteins and nucleic acids. Cambridge University Press.; see HMMER information at Washington University in St. Louis, Mo. The database also is extensively annotated and monitored by experts to enhance accuracy. A search was performed against the HMM database resulting in the identification of a "glycosyltransferase" domain in the amino acid sequence of human 33945 at about residues 445 to 577 of SEQ ID NO:2.

For further identification of domains in a 33945 protein sequence, and the determination that a polypeptide or protein of interest has a particular profile, the amino acid sequence of the protein can be searched against a database of domains, e.g., the ProDom database (Corpet et al. (1999), *Nucl. Acids Res.* 27:263–267) The ProDom protein domain database consists of an automatic compilation of homologous domains. Current versions of ProDom are built using recursive PSI-BLAST searches (Altschul S F et al. (1997) *Nucleic Acids Res.* 25:3389–3402; Gouzy et al. (1999) *Computers and Chemistry* 23:333–340.) of the SWISS-PROT 38 and TREMBL protein databases. The database automatically generates a consensus sequence for each domain. A BLAST search was performed against the HMM database resulting in the identification of a "ProDom family PD003162, "N-acetylgalactosaminyltransferase Transferase Polypeptide Acetylgalactosaminyltransferase UDP-GalNac:polypeptide Glycosyltransferase Protein-UDP-protein-UDP N-;" (SEQ ID NO:7) domain in the amino acid sequence of human 33945 at about residues 287 to 443 of SEQ ID NO:2.

A 33945 protein can further include a transmembrane domain at about amino acid residues 20 to 37 of SEQ ID NO:2. As used herein, the term "transmembrane domain" includes an amino acid sequence of about 5 amino acid residues in length that spans the plasma membrane. More preferably, a transmembrane domain includes about at least 10, 15, 20 or 22 amino acid residues and spans a membrane. Transmembrane domains are rich in hydrophobic residues, and typically have an alpha-helical structure. The presence of a transmembrane domain can be predicted by MEMSAT, (Jones et al., (1994) *Biochemistry* 33:3038–3049) and visualized in the hydropathy plot (FIG. 1) as a region mostly above the line for the preferred length of 15 to 25 amino acids. In a preferred embodiment, at least 50%, 60%, 70%, 80%, 90%, or 95% or more of the amino acids of a transmembrane domain are hydrophobic, e.g., leucines, isoleucines, tyrosines, or tryptophans. Transmembrane domains are described in Zagotta W. N. et al. (1996) *Annu. Rev. Neurosci.* 19: 235–263, the contents of which are incorporated herein by reference. Thus, amino acid residues 1 to about 19 and 38 to 581 of SEQ ID NO:2 comprise nontransmembrane regions of a 33945 protein.

Glycosyltransferases typically show a type II topology. Based on the sequence similarity between the glycosyltransferases and the 33945 polypeptides, the 33945 polypeptides are predicted to have a first nontransmembrane region, about amino acid residues 1 to 19 of SEQ ID NO:2, which is located in the cytoplasm, and a second nontransmembrane region, about amino acid residues 38 to 581 of SEQ ID NO:2 located outside the cytoplasm, e.g., in a vesicle, e.g. Golgi, lumen, or extracellularly. When located in the Golgi, a 33945 can glycosylate proteins destined for secretion while they mature. As an external membrane anchored protein, a 33945 can function as a cell adhesion molecule by binding a substrate, e.g., an oligosaccharide substrate located on an adjacent cell surface or in the extracellular matrix.

A 33945 glycosyltransferase can further include a leucine zipper motif or regions homologous with a leucine zipper motif. Leucine zippers typically contain a repeat of leucine positioned every seven amino acids (L-x(6)-L-x(6)-L-x(6)-L, SEQ ID NO:9), over a distance of eight helical turns. The segments containing these periodic arrays of leucines appear to exist in an alpha-helical conformation in which leucine side chains extending from one alpha helix interact with those from a similar alpha helix of a second polypeptide, facilitating dimerization. The leucine zipper pattern is present in many gene regulatory proteins, such as CCATT-box and enhancer binding protein (C/EBP), cAMP response element (CRE) binding proteins (CREB, CRE-BP1, ATFs), jun/AP1 family transcription factors, C-myc, L-myc and N-myc oncogenes and octamer-binding transcription factor 2 (Oct-2/OTF-2). These interactions are frequently required for the activity of the protein complex, e.g., transcriptional activation of a nucleic acid via binding to a gene regulatory sequence and subsequent formation of a transcription initiation complex. Leucine zippers therefore mediate protein-protein interactions in vivo and in particular, interactions between multi-subunit transcription factors (homodimers, heterodimers, etc.). The leucine zipper in the 33945 glycosyltransferase can be found at about amino acids 86 to 107 of SEQ ID NO:2.

Thus, in another embodiment, a 33945 glycosyltransferase or fragment or variant may have one or more activities of a leucine zipper motif, such as binding to another polypeptide that has a leucine zipper, for example, forming a dimer with a 33945 glycosyltransferase, or fragment or variant thereof containing a leucine zipper. The presence of a leucine zipper indicates that 33945 glycosyltransferase may participate in different pathways due to an ability to interact with different proteins via the leucine zipper. For example, it may be possible that a leucine zipper motif allows 33945 glycosyltransferase binding to a protein substrate which it may cleave. The presence of a leucine zipper motif may additionally confer regulation of one or more activities of 33945 glycosyltransferase modulated through binding to another protein or dissociation from the protein. In any event, it is likely that the leucine zipper modulates or is involved in one or more activities or functions of 33945 glycosyltransferase through its ability to confer binding of 33945 glycosyltransferase to a target molecule or binding partner. The term "leucine zipper activity," when used in reference to a protein, means a protein having one or more activities associated with leucine zipper function as described herein or otherwise known in the art.

A 33945 family member can include at least one RGD cell attachment site. As used herein, the term "RGD cell attachment site" refers to a cell adhesion sequence consisting of amino acids Arg-Gly-Asp found in extracellular matrix proteins and intracellular trafficking proteins (reviewed in Ruoslahti, E. (1996) *Annu. Rev. Cell Dev. Biol.* 12:697–715). An RGD sequence in a protein can mediate cell attachment through protein-protein interaction or can mediate interactions between proteins in cells or vesicles.

A 33945 family member can include at least one glycosyltransferase domain, at least one ricin domain, at least one transmembrane domain, at least one, preferably two nontransmembrane regions, at least one leucine zipper motif, and at least one RGD cell attachment site. Furthermore, a 33945 family member can include at least one, three, seven, preferably eleven protein kinase C phosphorylation sites (PS00005); at least one, three, five, eight, and preferably ten casein kinase II phosphorylation sites (PS00006); at least one cAMP- and cGMP-dependent protein kinase phosphorylation site (PS00004); at least one tyrosine kinase phosphorylation site (PS00007); at least one amidation site (PS00009); and at least one, three, five, and preferably eight N-myristoylation sites (PS00008).

As the 33945 polypeptides of the invention can modulate 33945-mediated activities, they can be useful for developing novel diagnostic and therapeutic agents for glycosyltransferase-associated or other 33945-associated, -mediated or related disorders, as described below. Based on the sequence similarities, the 33945 molecule of the present invention is predicted to have similar biological activities as glycosyltransferase family members.

Glycosyltransferases play roles in diverse cellular processes. For example, the major target of the natural IgM and IgG antibodies during hyperacute xenograft rejection is the terminal carbohydrate epitope Gal alpha(1,3)Gal, formed by the alpha 1,3-galactosyl transferase, which places a terminal galactose residue in an alpha-linkage to another galactose (Sandrin et al. (1994) *Immunol Rev* 141:169–90). As another example, mutations in the Piga gene, the protein product of which mediates N-acetylglucosamine attachment to phosphatidylinositol, results in the clonal hematologic disorder, paroxysmal nocturnal hemoglobinuria (Ware et al. (1994) *Blood* 83:2418–22). Additionally, UDP-galactose:ceramide galactosyltransferase is the enzyme responsible for the biosynthesis of galactosylceramide, a molecule thought to play a critical role in myelin formation, signal transduction, viral and microbial adhesion, and oligodendrocyte development (Kapitonov et al. (1999) *Glycobiology* 9:961–78).

Glycosylation of glycoproteins and glycolipids is one of many molecular changes that accompany malignant transformation. GlcNAc-branched N-glycans and terminal Lewis antigen sequences have been observed to increase in some cancers, and to correlate with poor prognosis (Dennis et al. (1999) *Biochim Biophys Acta* 1473:21–34). Cellular membrane over-expression and shedding of acidic glycosphingolipids into the interstitial spaces and blood of cancer patients may play a central role in increased tumour cell growth, lack of immune cell recognition and neovascularization and could represent a molecular target for cancer therapy (Fish (1996) *Med Hypotheses* 46:140–44).

As used herein, a "33945 activity", "biological activity of 33945" or "functional activity of 33945", refers to an activity exerted by a 33945 protein, polypeptide or nucleic acid molecule on e.g., a 33945-responsive cell or on a 33945 substrate, e.g., a lipid, protein, heterocyclic compound, or carbohydrate residue, as determined in vivo or in vitro. In one embodiment, a 33945 activity is a direct activity, such as an association with a 33945 target molecule. A "target molecule" or "binding partner" is a molecule with which a 33945 protein binds or interacts in nature, e.g., a lipid, protein, heterocyclic compound, or carbohydrate residue to which the 33945 protein attaches a carbohydrate moiety. In an exemplary embodiment, 33945 is an enzyme used for the glycosylation of a polypeptide substrate.

A 33945 activity can also be an indirect activity, e.g., a cellular signaling activity mediated by interaction of the 33945 protein with a 33945 ligand. Based on the above-described sequence structures and similarities to molecules of known function, the 33945 molecules of the present invention have similar biological activities as glycosyltransferase family members. For example, the 33945 protein of the present invention can have one or more of the following activities: 1) the ability to attach to a membrane; (2) the ability to interact with a substrate or target molecule; (3) the ability to transfer a sugar residue, e.g., an activated sugar residue to an acceptor molecule; (4) the ability to modulate the processing, folding, or secretion of proteins; (5) the ability to modulate proliferation, differentiation and/or function of endothelial cells, e.g., umbilical vein endothelial cells, cardiac microvascular endothelial cells; (6) the ability to modulate tumor cell growth and invasion; (7) the ability to modulate myelin formation; (8) the ability to modulate signal transduction; (9) the ability to modulate viral and microbial adhesion; (10) the ability to modulate oligodendrocyte development; (11) the ability to modulate sperm-egg binding; (12) the ability to modulate evasion of immune detection; (13) the ability to modulate xenograft rejection; or (14) the ability to antagonize or inhibit, competitively or non-competitively, any of 1–13.

The 33945 molecules of the invention can modulate the activities of cells in tissues where they are expressed. For example, 33945 mRNA is expressed at high levels in coronary smooth muscle cells and pancreas. In addition, there are differential levels of expression between tumors and their corresponding normal tissue, e.g. a high level of 33945 expression in colon tumor with a medium amount of expression in normal colon; a medium amount of 33945 expression in lung tumor tissue, and a low amount in normal lung. Accordingly, the 33945 molecules of the invention can act as therapeutic or diagnostic agents for cardiovascular disorders, e.g., atherosclerosis or endothelial cell disorders, pancreatic disorders, or cellular proliferative and/or differentiative disorders, as well as disorders related to tissues where 33945 mRNA is expressed at lower levels as described below. Further tests of 33945 expression found significant expression in situations characteristic of high amounts of angiogenesis, e.g., in fetal kidney, in Wilm's tumor of the kidney and in squamous cell carcinoma of the cervix. Medium amounts of 33945 expression also were found in kidney, brain cortex, inflammatory bowel disease colon tissue, and normal small intestine. Small amounts of 33945 expression also were found in normal artery, diseased aorta, human umbilical vein endothelial cells, skeletal muscle, breast tumor, prostate tumor, chronic obstructive pulmonary disease lung tissue, decubitus skin tissue, and megakaryocytes. Trace amounts of 33945 expression also were found in hemangioma, congestive heart failure heart tissue, normal adipose, normal spinal cord, differentiated osteoclasts, hypothalamus, normal breast, normal prostate, normal lymph node, normal tonsil, synovium, and activated peripheral blood monocytes.

The 33945 molecules can be used to treat cardiovascular disorders, e.g., atherosclerosis, in part because the 33945 mRNA is expressed in coronary smooth muscle cells or e.g., endothelial cell or angiogenesis disorders, in part because 33945 mRNA expression increases over control levels in tissues undergoing high amounts of angiogenesis, in cultured endothelial cells undergoing high rates of proliferation and in cultured endothelial cells stimulated by interferon gamma. As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as atherosclerosis, arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, atrial fibrillation, long-QT syndrome, congestive heart failure, sinus node dysfunction, angina, heart failure, hypertension, atrial fibrillation, atrial flutter, cardiomyopathiues, e.g., dilated cardiomyopathy or idiopathic cardiomyopathy, myocardial infarction, coronary artery disease, coronary artery spasm, ischemic disease, arrhythmia, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovasular disease or disorder also includes an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. As used herein, an "angiogenic disorder" includes a disease or disorder which affects or is caused by aberrant or deficient angiogenesis. Disorders involving angiogenesis include, but are not limited to, aberrant or excess angiogenesis in tumors such as hemangiomas and Kaposi's sarcoma, von Hippel-Lindau disease, as well as the angiogenesis associated with tumor growth; aberrant or excess angiogenesis in diseases such as a Castleman's disease or fibrodysplasia ossificans progressiva; aberrant or deficient angiogenesis associated with aging, complications of healing certain wounds and complications of diseases such as diabetes and rheumatoid arthritis; or aberrant or deficient angiogenesis associated with hereditary hemorrhagic telangiectasia, autosomal dominant polycystic kidney disease, myelodysplastic syndrome or Klippel-Trenaunay-Weber syndrome. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

The 33945 molecules can be used to treat pancreatic disorders, in part because the 33945 mRNA is expressed in the pancreas. Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

The 33945 molecules can be used to treat cellular proliferative and/or differentiative disorders, in part because the 33945 mRNA is expressed at differential levels between tumors and their corresponding normal tissue, e.g. a high level of 33945 expression in colon tumor with a medium amount of expression in normal colon; a medium amount of 33945 expression in lung tumor tissue, and a low amount in normal lung. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 33945 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Thus, the 33945 molecules can act as novel diagnostic targets and therapeutic agents for controlling one or more cardiovascular disorders, e.g., atherosclerosis or endothelial cell disorders, pancreatic disorders, cellular proliferative and/or differentiative disorders or other glycosyltransferase disorders. As used herein, "glycosyltransferase disorders" are diseases or disorders whose pathogenesis is caused by, is related to, or is associated with aberrant or deficient glycosyltransferase protein function or expression. Glycosyltransferase disorders can involve protein glycosylation, cellular adhesion, cellular proliferation or differentiation. Examples of such disorders, e.g., glycosyltransferase-associated disorders, include but are not limited to, cardiovascular disorders, e.g., atherosclerosis or endothelial cell disorders, pancreatic disorders, cellular proliferative and/or differentiative disorders as described above, as well as immune disorders, e.g., inflammatory disorders, viral diseases, and liver disorders.

The 33945 nucleic acid and protein of the invention can be used to treat and/or diagnose a variety of immune, e.g., inflammatory, (e.g. respiratory inflammatory) disorders in part because aberrant or deficient function or expression of glycosyltransferase family members can result in disorders of the immune system. Examples of immune and inflammatory disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

The 33945 nucleic acid and protein of the invention can be used to treat and/or diagnose a variety of viral disorders in part because aberrant or deficient function or expression of glycosyltransferase family members can involve protein glycosylation or cellular adhesion. Additionally, 33945 molecules can play an important role in the etiology of certain viral diseases, including but not limited to Hepatitis B, Hepatitis C and Herpes Simplex Virus (HSV). Modulators of 33945 activity could be used to control viral diseases. The modulators can be used in the treatment and/or diagnosis of viral infected tissue or virus-associated tissue fibrosis, especially liver and liver fibrosis. Also, 33945 modulators can be used in the treatment and/or diagnosis of virus-associated carcinoma, especially hepatocellular cancer.

The 33945 nucleic acid and protein of the invention can be used to treat and/or diagnose a variety of liver disorders in part because aberrant or deficient function or expression of glycosyltransferase family members can result in disorders of the hepatic system. Disorders which can be treated or diagnosed by the methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

The 33945 protein, fragments thereof, and derivatives and other variants of the sequence in SEQ ID NO:2 thereof are collectively referred to as "polypeptides or proteins of the invention" or "33945 polypeptides or proteins". Nucleic acid molecules encoding such polypeptides or proteins are collectively referred to as "nucleic acids of the invention" or "33945 nucleic acids." 33945 molecules refer to 33945 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, New York, 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6× SSC at about 45° C., followed by one or more washes in 0.2× SSC, 0.1% SDS at 60° C.; 3) high stringency hybridization conditions in 6× SSC at about 45° C., followed by one or more washes in 0.2× SSC, 0.1% SDS at 65° C.; and preferably 4) very high stringency hybridization conditions are 0.5M sodium phosphate, 7% SDS at 65° C., followed by one or more washes at 0.2× SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 33945 protein, preferably a mammalian 33945 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 33945 protein having less than about 30%, 20%, 10% and more preferably 5% (by dry weight), of non-33945 protein (also referred to herein as a "contaminating protein"), or of chemical precursors or non-33945 chemicals. When the 33945 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 33945 (e.g., the sequence of SEQ ID NO:1 or 3) without abolishing or more preferably, without substantially altering a biological activity, whereas an "essential" amino acid residue results in such a change. For example, amino acid residues that are conserved among the polypeptides of the present invention, e.g., those present in the glycosyltransferase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 33945 protein is preferably replaced with another amino acid residue from the same side chain family. Alternatively, in another embodiment, mutations can be introduced randomly along all or part of a 33945 coding sequence, such as by saturation mutagenesis, and the resultant mutants can be screened for 33945 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 33945 protein includes a fragment of a 33945 protein which participates in an interaction between a 33945 molecule and a non-33945 molecule. Biologically active portions of a 33945 protein include peptides comprising amino acid sequences sufficiently homologous to or derived from the amino acid sequence of the 33945 protein, e.g., the amino acid sequence shown in SEQ ID NO:2, which include fewer amino acids than the full length 33945 protein, and exhibit at least one activity of a 33945 protein. Typically, biologically active portions comprise a domain or motif with at least one activity of the 33945 protein, e.g., glycosylation of a polypeptide. A biologically active portion of a 33945 protein can be a polypeptide which is, for example, 10, 25, 50, 100, 200 or more amino acids in length. Biologically active portions of a 33945 protein can be used as targets for developing agents which modulate a 33945 mediated activity, e.g., glycosyltransferase activity.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 33945 amino acid sequence of SEQ ID NO:2 having 581 amino acid residues, at least [30%] 174, preferably at least [40%] 232, more preferably at least [50%] 290, even more preferably at least [60%] 348, and even more preferably at least [70%] 406, [80%] 464, or [90%] 522 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at the bioinformatics page of the website maintained by Accelrys, Inc., San Diego. Calif. USA), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 2 15:403–10. BLAST nucleotide searches can be performed with the NBLAST program, score=100, wordlength=12 to obtain nucleotide sequences homologous to 33945 nucleic acid molecules of the invention. BLAST protein searches can be performed with the XBLAST program, score=50, wordlength=3 to obtain amino acid sequences homologous to 33945 protein molecules of the invention. To obtain gapped alignments for comparison purposes, Gapped BLAST can be utilized as described in Altschul et at, (1997) *Nucleic Acids Res.* 25:33 89–3402. When utilizing BLAST and Gapped BLAST programs, the default parameters of the respective programs (e.g., XBLAST and NBLAST) can be used (accessible at the website maintained by National Center for Biotechnology Information. Bethesda. Md. USA).

Particular 33945 polypeptides of the present invention have an amino acid sequence sufficiently identical to the amino acid sequence of SEQ ID NO:2. The term "substantially identical" is used herein to refer to a first amino acid sequence that contains a sufficient or minimum number of identical or equivalent (e.g., with a similar side chain) amino acid residues to a second amino acid sequence such that the first and second amino acid sequences have a common structural domain or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity are defined herein as sufficiently or substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences have a common functional activity or encode a common structural polypeptide fold or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 33945 polypeptide described herein, e.g., a full length 33945 protein or a fragment thereof, e.g., a biologically active portion of 33945 protein. Also included is a nucleic acid fragment suitable for use as a hybridization probe, which can be used, e.g., to identify a nucleic acid molecule encoding a polypeptide of the invention, 33945 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of this nucleotide sequence. In one embodiment, the nucleic acid molecule includes sequences encoding the human 33945 protein (i.e., "the coding region" of SEQ ID NO:1, as shown in SEQ ID NO:3), as well as 5' untranslated sequences (nucleotides 1 to 80 of SEQ ID NO:1) and 3' untranslated sequences (nucleotides 1826 to 2850 of SEQ ID NO:1). Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 139 to 322 of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

33945 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a 33945 protein, e.g., an immunogenic or biologically active portion of a 33945 protein. A fragment can comprise those nucleotides of SEQ ID NO:1, which encode a glycosyltransferase domain of human 33945. The nucleotide sequence determined from the cloning of the 33945 gene allows for the generation of probes and primers designed for use in identifying and/or cloning other 33945 family members, or fragments thereof, as well as 33945 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100, 150, 200, 250, preferably 285 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 33945 nucleic acid fragment can include a sequence corresponding to a glycosyltransferase domain.

33945 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a glycosyltransferase domain (e.g., about amino acid residues 139 to 322 of SEQ ID NO:2); a ricin domain (e.g., about amino acid residues 441 to 577 of SEQ ID NO:2); and a transmembrane domain (e.g., about amino acid residues 20 to 37 of SEQ ID NO:2).

In another embodiment a set of primers is provided, e.g., primers suitable for use in a PCR, which can be used to amplify a selected region of a 33945 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a glycosyltransferase domain from about amino acid 139 to 322 of SEQ ID NO:2; a ricin domain from about amino acid residues 441 to 577 of SEQ ID NO:2; and a transmembrane domain from about amino acid residues 20 to 37 of SEQ ID NO:2.

A nucleic acid fragment can encode an epitope bearing region of a polypeptide described herein.

A nucleic acid fragment encoding a "biologically active portion of a 33945 polypeptide" can be prepared by isolating a portion of the nucleotide sequence of SEQ ID NO:1 or 3, which encodes a polypeptide having a 33945 biological activity (e.g., the biological activities of the 33945 proteins are described herein), expressing the encoded portion of the 33945 protein (e.g., by recombinant expression in vitro) and assessing the activity of the encoded portion of the 33945 protein. For example, a nucleic acid fragment encoding a biologically active portion of 33945 includes a glycosyltransferase domain, e.g., amino acid residues about 139 to 322 of SEQ ID NO:2. A nucleic acid fragment encoding a biologically active portion of a 33945 polypeptide, can comprise a nucleotide sequence which is greater than 300, 500, 700, preferably, 855 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800 or more nucleotides in length and hybridizes under stringent hybridization conditions to a nucleic acid molecule of SEQ ID NO:1 or SEQ ID NO:3.

33945 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 33945 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under stringent conditions, to the nucleotide sequence shown in SEQ ID NO 2 or a fragment of the sequence. Nucleic acid molecules corresponding to orthologs, homologs, and allelic variants of the 33945 cDNAs of the invention can further be isolated by mapping to the same chromosome or locus as the 33945 gene.

Preferred variants include those that are correlated with glycosylation of polypeptides.

Allelic variants of 33945, e.g., human 33945, include both functional and non-functional proteins. Functional allelic variants are naturally occurring amino acid sequence variants of the 33945 protein within a population that maintain 1) the ability to attach to a membrane; (2) the ability to interact with a substrate or target molecule; (3) the ability to transfer a sugar residue, e.g., an activated sugar residue, to an acceptor molecule; (4) the ability to modulate the processing, folding, or secretion of proteins; (5) the ability to modulate proliferation, differentiation and/or function of endothelial cells, e.g., umbilical vein endothelial cells, cardiac microvascular endothelial cells; (6) the ability to modulate tumor cell growth and invasion; (7) the ability to modulate myelin formation; (8) the ability to modulate signal transduction; (9) the ability to modulate viral and microbial adhesion; (10) the ability to modulate oligodendrocyte development; (11) the ability to modulate sperm-egg binding; (12) the ability to modulate evasion of immune detection; (13) the ability to modulate xenograft rejection; and (14) the ability to antagonize or inhibit, competitively or non-competitively, any of 1–13. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 33945, e.g., human 33945, protein within a population that do not have the ability to 1) the ability to attach to a membrane; (2) the ability to interact with a substrate or target molecule; (3) the ability to transfer an activated sugar residue to an acceptor molecule; (4) the ability to modulate the processing, folding, or secretion of proteins; (5) the ability to modulate proliferation, differentiation and/or function of endothelial cells, e.g., umbilical vein endothelial cells, cardiac microvascular endothelial cells; (6) the ability to modulate tumor cell growth and invasion; (7) the ability to modulate myelin formation; (8) the ability to modulate signal transduction; (9) the ability to modulate viral and microbial adhesion; (10) the ability to modulate oligodendrocyte development; (11) the ability to modulate sperm-egg binding; (12) the ability to modulate evasion of immune detection; (13) the ability to modulate xenograft rejection; and (14) the ability to antagonize or inhibit, competitively or non-competitively, any of 1–13. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 33945 family members and, thus, which have a nucleotide sequence which differs from the 33945 sequences of SEQ ID NO:1 or SEQ ID NO:3 are intended to be within the scope of the invention.

Antisense Nucleic Acid Molecules, Ribozymes and Modified 33945 Nucleic Acid Molecules In another aspect, the invention features, an isolated nucleic acid molecule which is antisense to 33945. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 33945 coding strand, or to only a portion thereof (e.g., the coding region of human 33945 corresponding to SEQ ID NO:3). In another embodiment, the antisense nucleic acid molecule is antisense to a "noncoding region" of the coding strand of a nucleotide sequence encoding 33945 (e.g., the 5' and 3' untranslated regions).

An antisense nucleic acid can be designed such that it is complementary to the entire coding region of 33945 mRNA, but more preferably is an oligonucleotide which is antisense to only a portion of the coding or noncoding region of 33945 mRNA. For example, the antisense oligonucleotide can be complementary to the region surrounding the translation start site of 33945 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 33945 protein to thereby inhibit expression of the protein, e.g., by inhibiting transcription and/or translation.

Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 33945-encoding nucleic acid can include one or more sequences complementary to the nucleotide sequence of a 33945 cDNA disclosed herein (i.e., SEQ ID NO:1 or SEQ ID NO:3), and a sequence having known catalytic sequence responsible for mRNA cleavage (see U.S. Pat. No. 5,093,246 or Haseloff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 33945-encoding mRNA. See, e.g., Cech et al. U.S. Pat. No. 4,987,071; and Cech et al. U.S. Pat. No. 5,116,742. Alternatively, 33945 mRNA can be used to select a catalytic RNA having a specific ribonuclease activity from a pool of RNA molecules. See, e.g., Bartel, D. and Szostak, J. W. (1993) *Science* 261:1411–1418.

33945 gene expression can be inhibited by targeting nucleotide sequences complementary to the regulatory region of the 33945 (e.g., the 33945 promoter and/or enhancers) to form triple helical structures that prevent transcription of the 33945 gene in target cells. See generally, Helene, C. (1991) *Anticancer Drug Des.* 6:569–84; Helene, C. (1992) *Ann. N.Y. Acad. Sci.* 660:27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 33945 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et a.l (1996) *Proc. Natl. Acad. Sci.* 93: 14670–675.

PNAs of 33945 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 33945 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 33945 nucleic acid of the invention, two complementary regions one having a fluorophore and one a quencher such that the molecular beacon is useful for quantitating the presence of the 33945 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 33945 Polypeptides

In another aspect, the invention features, an isolated 33945 protein, or fragment, e.g., a biologically active portion, for use as immunogens or antigens to raise or test (or more generally to bind) anti-33945 antibodies. 33945 protein can be isolated from cells or tissue sources using standard protein purification techniques. 33945 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present in a native cell.

In a preferred embodiment, a 33945 polypeptide has one or more of the following characteristics:

it has the ability to glycosylate a polypeptide;

it has a molecular weight, e.g., a deduced molecular weight, preferably ignoring any contribution of post translational modifications, amino acid composition or other physical characteristic of SEQ ID NO:2;

it has an overall sequence similarity of at least 60%, preferably at least 70%, more preferably at least 80, 90, or 95%, with a polypeptide of SEQ ID NO:2;

it can be found in the adrenal gland, brain, breast, colon, testis, or metastases from colon to liver;

it has a glycosyltransferase domain which is preferably about 70%, 80%, 90% or 95% with amino acid residues about 139 to 322 of SEQ ID NO:2;

it has a ricin domain which is preferably about 70%, 80%, 90% or 95% with amino acid residues about 441 to 577 of SEQ ID NO:2;

it has a transmembrane domain which is preferably about 70%, 80%, 90% or 95% with amino acid residues about 20 to 37 of SEQ ID NO:2; and it can be found with high levels of expression in coronary smooth muscle cells and pancreas and at differential levels of expression between tumors and their corresponding normal tissue, e.g. a high level of 33945 expression in colon tumor with a medium amount of expression in normal colon; a medium amount of 33945 expression in lung tumor tissue, and a low amount in normal lung;

its expression can increase over control levels in tissues undergoing high amounts of angiogenesis, in cultured endothelial cells undergoing high rates of proliferation and in cultured endothelial cells stimulated by interferon gamma.

In a preferred embodiment the 33945 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the glycosyltransferase domain about 139 to 322 of SEQ ID NO:2. In another embodiment one or more differences are in the glycosyltransferase domain about 139 to 322 of SEQ ID NO:2.

Other embodiments include a protein that contains one or more changes in amino acid sequence, e.g., a change in an amino acid residue which is not essential for activity. Such 33945 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2. In another embodiment, the protein includes fragments or regions homologous to fragments, at least about 70%, 80%, 90%, 95%, 96%, 97%, 98%, 99% or more homologous to a fragment of SEQ ID NO:2. A fragment of an 33945 protein can be a domain, e.g. a glycosyltransferase domain or a fragment thereof, e.g. about amino acid residues 139 to 200, 201 to 270, or 271 to 322 of SEQ ID NO:2. Alternatively, a fragment of an 33945 protein can be a domain plus surrounding sequence, e.g., about amino acids 100 to 385 or 130 to 415 of SEQ ID NO:2.

A 33945 protein or fragment is provided which varies from the sequence of SEQ ID NO:2 in regions defined by amino acids about 325 to 435 by at least one but by less than 15, 10 or 5 amino acid residues in the protein or fragment but which does not differ from SEQ ID NO:2 in regions defined by amino acids about 139 to 322. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 33945 protein includes a glycosyltransferase domain. Moreover, other biologically active portions, in which other regions of the protein are deleted, can be prepared by recombinant techniques and evaluated for one or more of the functional activities of a native 33945 protein.

In a preferred embodiment, the 33945 protein has an amino acid sequence shown in SEQ ID NO:2. In other embodiments, the 33945 protein is sufficiently or substantially identical to SEQ ID NO:2. In yet another embodiment, the 33945 protein is sufficiently or substantially identical to SEQ ID NO:2 and retains the functional activity of the protein of SEQ ID NO:2, as described in detail in the subsections above.

33945 Chimeric or Fusion Proteins

In another aspect, the invention provides 33945 chimeric or fusion proteins. As used herein, a 33945 "chimeric protein" or "fusion protein" includes a 33945 polypeptide linked to a non-33945 polypeptide. A "non-33945 polypeptide" refers to a polypeptide having an amino acid sequence corresponding to a protein which is not substantially homologous to the 33945 protein, e.g., a protein which is different from the 33945 protein and which is derived from the same or a different organism. The 33945 polypeptide of the fusion protein can correspond to all or a portion e.g., a fragment described herein of a 33945 amino acid sequence. In a preferred embodiment, a 33945 fusion protein includes at least one (or two) biologically active portion of a 33945 protein. The non-33945 polypeptide can be fused to the N-terminus or C-terminus of the 33945 polypeptide.

The fusion protein can include a moiety which has a high affinity for a ligand. For example, the fusion protein can be a GST-33945 fusion protein in which the 33945 sequences are fused to the C-terminus of the GST sequences. Such fusion proteins can facilitate the purification of recombinant 33945. Alternatively, the fusion protein can be a 33945 protein containing a heterologous signal sequence at its N-terminus. In certain host cells (e.g., mammalian host cells), expression and/or secretion of 33945 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge Cl and C2 sequences of an immunoglobulin or human serum albumin.

The 33945 fusion proteins of the invention can be incorporated into pharmaceutical compositions and administered to a subject in vivo. The 33945 fusion proteins can be used to modulate the bioavailability of a 33945 substrate. 33945 fusion proteins can be useful therapeutically for the treatment of disorders caused by, for example, (i) aberrant modification or mutation of a gene encoding a 33945 protein; (ii) mis-regulation of the 33945 gene; and (iii) aberrant post-translational modification of a 33945 protein.

Moreover, the 33945-fusion proteins of the invention can be used as immunogens to produce anti-33945 antibodies in a subject, to purify 33945 ligands and in screening assays to identify molecules which inhibit the interaction of 33945 with a 33945 substrate.

Expression vectors are commercially available that already encode a fusion moiety (e.g., a GST polypeptide). A 33945-encoding nucleic acid can be cloned into such an expression vector such that the fusion moiety is linked in-frame to the 33945 protein.

Variants of 33945 Proteins

In another aspect, the invention also features a variant of a 33945 polypeptide, e.g., which functions as an agonist (mimetics) or as an antagonist. Variants of the 33945 proteins can be generated by mutagenesis, e.g., discrete point mutation, the insertion or deletion of sequences or the truncation of a 33945 protein. An agonist of the 33945 proteins can retain substantially the same, or a subset, of the biological activities of the naturally occurring form of a 33945 protein. An antagonist of a 33945 protein can inhibit one or more of the activities of the naturally occurring form of the 33945 protein by, for example, competitively modulating a 33945-mediated activity of a 33945 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 33945 protein.

Variants of a 33945 protein can be identified by screening combinatorial libraries of mutants, e.g., truncation mutants, of a 33945 protein for agonist or antagonist activity.

Libraries of fragments e.g., N terminal, C terminal, or internal fragments, of a 33945 protein coding sequence can be used to generate a variegated population of fragments for screening and subsequent selection of variants of a 33945 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 33945 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 33945 library. For example, a library of expression vectors can be transfected into a cell line, e.g., a cell line, which ordinarily responds to 33945 in a substrate-dependent manner. The transfected cells are then contacted with 33945 and the effect of the expression of the mutant on signaling by the 33945 substrate can be detected, e.g., by measuring glycosylation of a polypeptide. Plasmid DNA can then be recovered from the cells which score for inhibition, or alternatively, potentiation of signaling by the 33945 substrate, and the individual clones further characterized.

In another aspect, the invention features a method of making a 33945 polypeptide, e.g., a peptide having a non-wild type activity, e.g., an antagonist, agonist, or super agonist of a naturally occurring 33945 polypeptide, e.g., a naturally occurring 33945 polypeptide. The method includes altering the sequence of a 33945 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 33945 polypeptide a biological activity of a naturally occurring 33945 polypeptide. The method includes altering the sequence, e.g., by substitution or deletion of one or more residues, of a 33945 polypeptide, e.g., altering the sequence of a non-conserved region, or a domain or residue described herein, and testing the altered polypeptide for the desired activity.

Anti-33945 Antibodies

In another aspect, the invention provides an anti-33945 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and $F(ab')_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 33945 protein or, antigenic peptide fragment of 33945 can be used as an immunogen or can be used to identify anti-33945 antibodies made with other immunogens, e.g., cells, membrane preparations, and the like. The antigenic peptide of 33945 should include at least 8 amino acid residues of the amino acid sequence shown in SEQ ID NO:2 and encompasses an epitope of 33945. Preferably, the antigenic peptide includes at least 10 amino acid residues, more preferably at least 15 amino acid residues, even more preferably at least 20 amino acid residues, and most preferably at least 30 amino acid residues.

Fragments of 33945 which include residues about 126 to 134, from about 175 to 186, and from about 534 to 546 can be used to make, e.g., used as immunogens or used to characterize the specificity of an antibody, antibodies against hydrophilic regions of the 33945 protein (see FIG. 1). Similarly, fragments of 33945 which include residues about 20 to 29, from about 30 to 37, and from about 251 to 257 can be used to make an antibody against a hydrophobic region of the 33945 protein; a fragment of 33945 which include residues about 145 to 160, about 180 to 200, or about 250 to 300 can be used to make an antibody against the glycosyltransferase region of the 33945 protein; and a fragment of 33945 which include residues about 445 to 460, about 480 to 500, or about 525 to 550 can be used to make an antibody against the ricin region of the 33945 protein.

Antibodies reactive with, or specific or selective for, any of these regions, or other regions or domains described herein are provided.

Preferred epitopes encompassed by the antigenic peptide are regions of 33945 are located on the surface of the protein, e.g., hydrophilic regions, as well as regions with high antigenicity. For example, an Emini surface probability analysis of the human 33945 protein sequence can be used to indicate the regions that have a particularly high probability of being localized to the surface of the 33945 protein and are thus likely to constitute surface residues useful for targeting antibody production.

In a preferred embodiment the antibody binds an epitope on any domain or region on 33945 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, S. L. (1985) Science 229:1202–1207; Oi et al. (1986) BioTechniques 4:214; Winter U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12:899–903).

The anti-33945 antibody can be a single chain antibody. A single-chain antibody (scFV) can be engineered (see, for example, Colcher, D. et al. (1999) Ann. N Y Acad. Sci. 880:263–80; and Reiter, Y. (1996) Clin. Cancer Res. 2:245–52). The single chain antibody can be dimerized or multimerized to generate multivalent antibodies having specificities for different epitopes of the same target 33945 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208, 020), CC-1065 (see US Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-33945 antibody (e.g., monoclonal antibody) can be used to isolate 33945 by standard techniques, such as affinity chromatography or immunoprecipitation. Moreover, an anti-33945 antibody can be used to detect 33945 protein (e.g., in a cellular lysate or cell supernatant) in order to evaluate the abundance and pattern of expression of the protein. Anti-33945 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 33945 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 33945 proteins, mutant forms of 33945 proteins, fusion proteins, and the like).

The recombinant expression vectors of the invention can be designed for expression of 33945 proteins in prokaryotic or eukaryotic cells. For example, polypeptides of the invention can be expressed in *E. coli,* insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 33945 activity assays, (e.g., direct assays or competitive assays described in detail below), or to generate antibodies specific or selective for 33945 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 33945 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., (1986) *Reviews*-Trends in Genetics 1:1.

Another aspect the invention provides a host cell which includes a nucleic acid molecule described herein, e.g., a 33945 nucleic acid molecule within a recombinant expression vector or a 33945 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 33945 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 33945 protein. Accordingly, the invention further provides methods for producing a 33945 protein using the host cells of the invention. In one embodiment, the method includes culturing the host cell of the invention (into which a recombinant expression vector encoding a 33945 protein has been introduced) in a suitable medium such that a 33945 protein is produced. In another embodiment, the method further includes isolating a 33945 protein from the medium or the host cell.

In another aspect, the invention features, a cell or purified preparation of cells which include a 33945 transgene, or which otherwise misexpress 33945. The cell preparation can consist of human or non-human cells, e.g., rodent cells, e.g., mouse or rat cells, rabbit cells, or pig cells. In preferred embodiments, the cell or cells include a 33945 transgene, e.g., a heterologous form of 33945, e.g., a gene derived from humans (in the case of a non-human cell). The 33945 transgene can be misexpressed, e.g., overexpressed or underexpressed. In other preferred embodiments, the cell or cells include a gene which misexpresses an endogenous 33945, e.g., a gene the expression of which is disrupted, e.g., a knockout. Such cells can serve as a model for studying disorders which are related to mutated or misexpressed 33945 alleles or for use in drug screening.

In another aspect, the invention features, a human cell, e.g., a hematopoietic stem cell, transformed with nucleic acid which encodes a subject 33945 polypeptide.

Also provided are cells, preferably human cells, e.g., human hematopoietic or fibroblast cells, in which an endogenous 33945 is under the control of a regulatory sequence that does not normally control the expression of the endogenous 33945 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 33945 gene. For example, an endogenous 33945 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 33945 protein and for identifying and/or evaluating modulators of 33945 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 33945 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 33945 protein to particular cells. A transgenic founder animal can be identified based upon the presence of a 33945 transgene in its genome and/or expression of 33945 mRNA in tissues or cells of the animals. A transgenic founder animal can then be used to breed additional animals carrying the transgene. Moreover, transgenic animals carrying a transgene encoding a 33945 protein can further be bred to other transgenic animals carrying other transgenes.

33945 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 33945 protein (e.g., via a recombinant expression vector in a host cell in gene therapy applications), to detect a 33945 mRNA (e.g., in a biological sample) or a genetic alteration in a 33945 gene, and to modulate 33945 activity, as described further below. The 33945 proteins can be used to treat disorders characterized by insufficient or excessive production of a 33945 substrate or production of 33945 inhibitors. In addition, the 33945 proteins can be used to screen for naturally occurring 33945 substrates, to screen for drugs or compounds which modulate 33945 activity, as well as to treat disorders characterized by insufficient or excessive production of 33945 protein or production of 33945 protein forms which have decreased, aberrant or unwanted activity compared to 33945 wild type protein (e.g., protein glycosylation, cellular adhesion, cellular proliferation or differentiation). Moreover, the anti-33945 antibodies of the invention can be used to detect and isolate 33945 proteins, regulate the bioavailability of 33945 proteins, and modulate 33945 activity.

A method of evaluating a compound for the ability to interact with, e.g., bind, a subject 33945 polypeptide is provided. The method includes: contacting the compound with the subject 33945 polypeptide; and evaluating ability of the compound to interact with, e.g., to bind or form a complex with the subject 33945 polypeptide. This method can be performed in vitro, e.g., in a cell free system, or in vivo, e.g., in a two-hybrid interaction trap assay. This method can be used to identify naturally occurring molecules which interact with subject 33945 polypeptide. It can also be used to find natural or synthetic inhibitors of subject 33945 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 33945 proteins, have a stimulatory or inhibitory effect on, for example, 33945 expression or 33945 activity, or have a stimulatory or inhibitory effect on, for example, the expression or activity of a 33945 substrate. Compounds thus identified can be used to modulate the activity of target gene products (e.g., 33945 genes) in a therapeutic protocol, to elaborate the biological function of the target gene product, or to identify compounds that disrupt normal target gene interactions.

In one embodiment, the invention provides assays for screening candidate or test compounds which are substrates of a 33945 protein or polypeptide or a biologically active portion thereof. In another embodiment, the invention provides assays for screening candidate or test compounds which bind to or modulate the activity of a 33945 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909–13; Erb et al. (1994) *Proc. Natl. Acad. Sci. USA* 91:11422–426; Zuckermann et al. (1994). *J. Med. Chem.* 37:2678–85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233–51.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 33945 protein or biologically active portion thereof is contacted with a test compound, and the ability of the test compound to modulate 33945 activity is determined. Determining the ability of the test compound to modulate 33945 activity can be accomplished by monitoring, for example, glycosylation of a polypeptide. The cell, for example, can be of mammalian origin, e.g., human.

The ability of the test compound to modulate 33945 binding to a compound, e.g., a 33945 substrate, or to bind to 33945 can also be evaluated. This can be accomplished, for example, by coupling the compound, e.g., the substrate, with a radioisotope or enzymatic label such that binding of the compound, e.g., the substrate, to 33945 can be determined by detecting the labeled compound, e.g., substrate, in a complex. Alternatively, 33945 could be coupled with a radioisotope or enzymatic label to monitor the ability of a test compound to modulate 33945 binding to a 33945 substrate in a complex. For example, compounds (e.g., 33945 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 33945 substrate) to interact with 33945 with or without the labeling of any of the interactants can be evaluated. For example, a microphysiometer can be used to detect the interaction of a compound with 33945 without the labeling of either the compound or the 33945. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 33945.

In yet another embodiment, a cell-free assay is provided in which a 33945 protein or biologically active portion thereof is contacted with a test compound and the ability of the test compound to bind to the 33945 protein or biologically active portion thereof is evaluated. Preferred biologically active portions of the 33945 proteins to be used in assays of the present invention include fragments which participate in interactions with non-33945 molecules, e.g., fragments with high surface probability scores.

Soluble and/or membrane-bound forms of isolated proteins (e.g., 33945 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 33945 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 33945, an anti-33945 antibody or its target molecule to facilitate separation of complexed from uncomplexed forms of one or both of the proteins, as well as to accommodate automation of the assay. Binding of a test compound to a 33945 protein, or interaction of a 33945 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/33945 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 33945 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 33945 binding or activity determined using standard techniques.

Other techniques for immobilizing either a 33945 protein or a target molecule on matrices include using conjugation of biotin and streptavidin. Biotinylated 33945 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 33945 protein or target molecules but which do not interfere with binding of the 33945 protein to its target molecule. Such antibodies can be derivatized to the wells of the plate, and unbound target or 33945 protein trapped in the wells by antibody conjugation. Methods for detecting such complexes, in addition to those described above for the GST-immobilized complexes, include immunodetection of complexes using antibodies reactive with the 33945 protein or target molecule, as well as enzyme-linked assays which rely on detecting an enzymatic activity associated with the 33945 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. (1999) *Current Protocols in Molecular Biology*, J. Wiley, N.Y.); and immunoprecipitation (see, for example, Ausubel, F. et al., eds. (1999) *Current Protocols in Molecular Biology*, J. Wiley, N.Y.). Such resins and chromatographic techniques are known to one skilled in the art (see, e.g., Heegaard, N. H., (1998) *J Mol Recognit* 11: 141–8; Hage, D. S., and Tweed, S. A. (1997) *J Chromatogr B Biomed Sci Appl.* 699:499–525). Further, fluorescence energy transfer can also be conveniently utilized, as described herein, to detect binding without further purification of the complex from solution.

In a preferred embodiment, the assay includes contacting the 33945 protein or biologically active portion thereof with a known compound which binds 33945 to form an assay mixture, contacting the assay mixture with a test compound, and determining the ability of the test compound to interact with a 33945 protein, wherein determining the ability of the test compound to interact with a 33945 protein includes determining the ability of the test compound to preferentially bind to 33945 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 33945 genes herein identified. In an alternative embodiment, the invention provides methods for determining the ability of the test compound to modulate the activity of a 33945 protein through modulation of the activity of a downstream effector of a 33945 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 33945 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 33945 ("33945-binding proteins" or "33945-bp") and are involved in 33945 activity. Such 33945-bps can be activators or inhibitors of signals by the 33945 proteins or 33945 targets as, for example, downstream elements of a 33945-mediated signaling pathway.

The two-hybrid system is based on the modular nature of most transcription factors, which consist of separable DNA-binding and activation domains. Briefly, the assay utilizes two different DNA constructs. In one construct, the gene that codes for a 33945 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 33945 protein can be the fused to the activator domain.) If the "bait" and the "prey" proteins are able to interact, in vivo, forming a 33945-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 33945 protein.

In another embodiment, modulators of 33945 expression are identified. For example, a cell or cell free mixture is contacted with a candidate compound and the expression of 33945 mRNA or protein evaluated relative to the level of expression of 33945 mRNA or protein in the absence of the candidate compound. When expression of 33945 mRNA or protein is greater in the presence of the candidate compound than in its absence, the candidate compound is identified as a stimulator of 33945 mRNA or protein expression. Alternatively, when expression of 33945 mRNA or protein is less (statistically significantly less) in the presence of the candidate compound than in its absence, the candidate compound is identified as an inhibitor of 33945 mRNA or protein expression. The level of 33945 mRNA or protein expression can be determined by methods described herein for detecting 33945 mRNA or protein.

In another aspect, the invention pertains to a combination of two or more of the assays described herein. For example, a modulating agent can be identified using a cell-based or a cell free assay, and the ability of the agent to modulate the activity of a 33945 protein can be confirmed in vivo, e.g., in an animal such as an animal model for protein glycosylation, cellular adhesion, atherosclerosis, endothelial cell disorders, cellular proliferation or differentiation disorders.

This invention further pertains to novel agents identified by the above-described screening assays. Accordingly, it is within the scope of this invention to further use an agent identified as described herein (e.g., a 33945 modulating agent, an antisense 33945 nucleic acid molecule, a 33945-specific antibody, or a 33945-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 33945 with a disease; (ii) identify an individual from a minute biological sample (tissue typing); and (iii) aid in forensic identification of a biological sample. These applications are described in the subsections below.

Chromosome Mapping

The 33945 nucleotide sequences or portions thereof can be used to map the location of the 33945 genes on a chromosome. This process is called chromosome mapping. Chromosome mapping is useful in correlating the 33945 sequences with genes associated with disease.

Briefly, 33945 genes can be mapped to chromosomes by preparing PCR primers (preferably 15–25 bp in length) from the 33945 nucleotide sequences. These primers can then be used for PCR screening of somatic cell hybrids containing individual human chromosomes. Only those hybrids containing the human gene corresponding to the 33945 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 33945 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man,* available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the 33945 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 33945 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 33945 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 33945 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 33945 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 33945 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 33945 probes can be used to identify tissue by species and/or by organ type.

In a similar fashion, these reagents, e.g., 33945 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 33945.

Such disorders include, e.g., a disorder associated with the misexpression of 33945 gene; a disorder of the cardiovascular system, pancreatic system, cellular proliferative or differentiative system, immune system, hepatic system or the protein glycosylation or cell adhesion system.

The method includes one or more of the following:

detecting, in a tissue of the subject, the presence or absence of a mutation which affects the expression of the 33945 gene, or detecting the presence or absence of a mutation in a region which controls the expression of the gene, e.g., a mutation in the 5' control region;

detecting, in a tissue of the subject, the presence or absence of a mutation which alters the structure of the 33945 gene;

detecting, in a tissue of the subject, the misexpression of the 33945 gene, at the mRNA level, e.g., detecting a non-wild type level of a mRNA;

detecting, in a tissue of the subject, the misexpression of the gene, at the protein level, e.g., detecting a non-wild type level of a 33945 polypeptide.

In preferred embodiments the method includes: ascertaining the existence of at least one of: a deletion of one or more nucleotides from the 33945 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 33945 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 33945 gene; the presence of a non-wild type splicing pattern of a messenger RNA transcript of the gene; or a non-wild type level of 33945.

Methods of the invention can be used prenatally or to determine if a subject's offspring will be at risk for a disorder.

In preferred embodiments the method includes determining the structure of a 33945 gene, an abnormal structure being indicative of risk for the disorder.

In preferred embodiments the method includes contacting a sample from the subject with an antibody to the 33945 protein or a nucleic acid, which hybridizes specifically with the gene. These and other embodiments are discussed below.

Diagnostic and Prognostic Assays

The presence, level, or absence of 33945 protein or nucleic acid in a biological sample can be evaluated by obtaining a biological sample from a test subject and contacting the biological sample with a compound or an agent capable of detecting 33945 protein or nucleic acid (e.g., mRNA, genomic DNA) that encodes 33945 protein such that the presence of 33945 protein or nucleic acid is detected in the biological sample. The term "biological sample" includes tissues, cells and biological fluids isolated from a subject, as well as tissues, cells and fluids present within a subject. A preferred biological sample is serum. The level of expression of the 33945 gene can be measured in a number of ways, including, but not limited to: measuring the mRNA encoded by the 33945 genes; measuring the amount of protein encoded by the 33945 genes; or measuring the activity of the protein encoded by the 33945 genes.

The level of mRNA corresponding to the 33945 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 33945 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 33945 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 33945 genes.

The level of mRNA in a sample that is encoded by one of 33945 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 33945 gene being analyzed.

In another embodiment, the methods further contacting a control sample with a compound or agent capable of detecting 33945 mRNA, or genomic DNA, and comparing the presence of 33945 mRNA or genomic DNA in the control sample with the presence of 33945 mRNA or genomic DNA in the test sample.

A variety of methods can be used to determine the level of protein encoded by 33945. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 33945 protein in a biological sample in vitro as well as in vivo. In vitro techniques for detection of 33945 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 33945 protein include introducing into a subject a labeled anti-33945 antibody. For example, the antibody can be labeled with a radioactive marker whose presence and location in a subject can be detected by standard imaging techniques.

In another embodiment, the methods further include contacting the control sample with a compound or agent capable of detecting 33945 protein, and comparing the presence of 33945 protein in the control sample with the presence of 33945 protein in the test sample.

The invention also includes kits for detecting the presence of 33945 in a biological sample. For example, the kit can include a compound or agent capable of detecting 33945 protein or mRNA in a biological sample; and a standard. The compound or agent can be packaged in a suitable container. The kit can further comprise instructions for using the kit to detect 33945 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 33945 expression or activity. As used herein, the term "unwanted" includes an unwanted phenomenon involved in a biological response such as pain or deregulated cell proliferation.

In one embodiment, a disease or disorder associated with aberrant or unwanted 33945 expression or activity is identified. A test sample is obtained from a subject and 33945 protein or nucleic acid (e.g., mRNA or genomic DNA) is evaluated, wherein the level, e.g., the presence or absence, of 33945 protein or nucleic acid is diagnostic for a subject having or at risk of developing a disease or disorder associated with aberrant or unwanted 33945 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 33945 expression or activity. For example, such methods can be used to determine whether a subject can be effectively treated with an agent for a cell protein glycosylation, cellular adhesion, atherosclerosis, an endothelial cell disorder, or a cellular proliferation or differentiation disorder.

The methods of the invention can also be used to detect genetic alterations in a 33945 gene, thereby determining if a subject with the altered gene is at risk for a disorder characterized by misregulation in 33945 protein activity or nucleic acid expression, such as a protein glycosylation, cellular adhesion, atherosclerosis, endothelial cell disorder, or cellular proliferation or differentiation disorder. In preferred embodiments, the methods include detecting, in a sample from the subject, the presence or absence of a genetic alteration characterized by at least one of an alteration affecting the integrity of a gene encoding a 33945-protein, or the mis-expression of the 33945 gene. For example, such genetic alterations can be detected by ascertaining the existence of at least one of 1) a deletion of one or more nucleotides from a 33945 gene; 2) an addition of one or more nucleotides to a 33945 gene; 3) a substitution of one or more nucleotides of a 33945 gene, 4) a chromosomal rearrangement of a 33945 gene; 5) an alteration in the level of a messenger RNA transcript of a 33945 gene, 6) aberrant modification of a 33945 gene, such as of the methylation pattern of the genomic DNA, 7) the presence of a non-wild type splicing pattern of a messenger RNA transcript of a 33945 gene, 8) a non-wild type level of a 33945-protein, 9) allelic loss of a 33945 gene, and 10) inappropriate post-translational modification of a 33945-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 33945-gene. This method can include the steps of collecting a sample of cells from a subject, isolating nucleic acid (e.g., genomic, mRNA or both) from the sample, contacting the nucleic acid sample with one or more primers which specifically hybridize to a 33945 gene under conditions such that hybridization and amplification of the 33945 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 33945 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 33945 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 33945 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 33945 gene and detect mutations by comparing the sequence of the sample 33945 with the corresponding wild-type (control) sequence. Automated sequencing procedures can be utilized when performing the diagnostic assays (Naeve C. W. et al. (1995) *Biotechniques* 19:448–53), including sequencing by mass spectrometry.

Other methods for detecting mutations in the 33945 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 33945 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 33945 genes.

For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 33945 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification can also be performed using Taq ligase for amplification (Barany (1991) *Proc. Natl. Acad. Sci USA* 88:189–93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 33945 gene.

Use of 33945 Molecules as Surrogate Markers

The 33945 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 33945 molecules of the invention can be detected, and can be correlated with one or more biological states in vivo. For example, the 33945 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 33945 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 33945 marker) transcription or expression, the amplified marker can be in a quantity which is more readily detectable than the drug itself. Also, the marker can be more easily detected due to the nature of the marker itself; for example, using the methods described herein, anti-33945 antibodies can be employed in an immune-based detection system for a 33945 protein marker, or 33945-specific radiolabeled probes can be used to detect a 33945 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

The 33945 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) Eur. J. Cancer 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 33945 protein or RNA) for specific tumor markers in a subject, a drug or course of treatment can be selected that is optimized for the treatment of the specific tumor likely to be present in the subject. Similarly, the presence or absence of a specific sequence mutation in 33945 DNA can correlate with a 33945 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-33945 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208, 020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted 33945 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 33945 molecules of the present invention or 33945 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 33945 expression or activity, by administering to the subject a 33945 or an agent which modulates 33945 expression or at least one 33945 activity. Subjects at risk for a disease which is caused or contributed to by aberrant or unwanted 33945 expression or activity can be identified by, for example, any or a combination of diagnostic or prognostic assays as described herein. Administration of a prophylactic agent can occur prior to the manifestation of symptoms characteristic of the 33945 aberrance, such that a disease or disorder is prevented or, alternatively, delayed in its progression. Depending on the type of 33945 aberrance, for example, a 33945, 33945 agonist or 33945 antagonist agent can be used for treating the subject. The appropriate agent can be determined based on screening assays described herein.

It is possible that some 33945 disorders can be caused, at least in part, by an abnormal level of gene product, or by the presence of a gene product exhibiting abnormal activity. As such, the reduction in the level and/or activity of such gene products would bring about the amelioration of disorder symptoms.

The 33945 molecules can act as novel diagnostic targets and therapeutic agents for controlling one or more of cardiovascular disorders, e.g., atherosclerosis or endothelial cell disorders, pancreatic disorders, cellular proliferative and/or differentiative disorders, immune disorders, e.g., inflammatory disorders, viral diseases, and liver disorders, all of which are described above. The molecules of the invention also can act as novel diagnostic targets and therapeutic agents for controlling one or more of disorders associated with bone metabolism, pain disorders and metabolic disorders.

"Bone metabolism" refers to direct or indirect effects in the formation or degeneration of bone structures, e.g., bone formation, bone resorption, etc., which can ultimately affect the concentrations in serum of calcium and phosphate. This term also includes activities mediated by 33945 molecules effects in bone cells, e.g. osteoclasts and osteoblasts, that can in turn result in bone formation and degeneration. For example, 33945 molecules can support different activities of bone resorbing osteoclasts such as the stimulation of differentiation of monocytes and mononuclear phagocytes into osteoclasts. Accordingly, 33945 molecules that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anticonvulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Additionally, 33945 can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) Pain, New York:McGraw-Hill); pain associated with musculoskeletal disorders, e.g., joint pain; tooth pain; headaches; pain associated with surgery; pain related to irritable bowel syndrome; or chest pain.

As discussed, successful treatment of 33945 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 33945 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 33945 expression is through the use of aptamer molecules specific for 33945 protein. Aptamers are nucleic acid molecules having a tertiary structure which permits them to specifically or selectively bind to protein ligands (see, e.g., Osborne, et al. (1997) Curr. Opin. Chem Biol. 1: 5–9; and Patel, D. J. (1997) Curr Opin Chem Biol 1:32–46). Since nucleic acid molecules can in many cases be more conveniently introduced into target cells than therapeutic protein molecules can be, aptamers offer a method by which 33945 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 33945 disorders. For a description of antibodies, see the Antibody section above.

In circumstances wherein injection of an animal or a human subject with a 33945 protein or epitope for stimulating antibody production is harmful to the subject, it is possible to generate an immune response against 33945 through the use of anti-idiotypic antibodies (see, for example, Herlyn, D. (1999) Ann Med 31:66–78; and Bhattacharya-Chatterjee, M., and Foon, K. A. (1998) Cancer Treat Res. 94:51–68). If an anti-idiotypic antibody is introduced into a mammal or human subject, it should stimulate the production of anti-anti-idiotypic antibodies, which should be specific to the 33945 protein. Vaccines directed to a disease characterized by 33945 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) Proc. Natl. Acad. Sci. USA 90:7889–7893).

The identified compounds that inhibit target gene expression, synthesis and/or activity can be administered to a patient at therapeutically effective doses to prevent, treat or ameliorate 33945 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques.

The compound which is able to modulate 33945 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) Current Opinion in Biotechnology 7:89–94 and in Shea, K. J. (1994) Trends in Polymer Science 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) Nature 361:645–647. Through the use of isotope-labeling, the "free" concentration of compound which modulates the expression or activity of 33945 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) Analytical Chemistry 67:2142–2144.

Another aspect of the invention pertains to methods of modulating 33945 expression or activity for therapeutic purposes. Accordingly, in an exemplary embodiment, the modulatory method of the invention involves contacting a cell with a 33945 or agent that modulates one or more of the activities of 33945 protein activity associated with the cell. An agent that modulates 33945 protein activity can be an agent as described herein, such as a nucleic acid or a protein, a naturally-occurring target molecule of a 33945 protein (e.g., a 33945 substrate or receptor), a 33945 antibody, a 33945 agonist or antagonist, a peptidomimetic of a 33945 agonist or antagonist, or other small molecule.

In one embodiment, the agent stimulates one or 33945 activities. Examples of such stimulatory agents include active 33945 protein and a nucleic acid molecule encoding 33945. In another embodiment, the agent inhibits one or more 33945 activities. Examples of such inhibitory agents include antisense 33945 nucleic acid molecules, anti33945 antibodies, and 33945 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 33945 protein or nucleic acid molecule. In one embodiment, the method involves administering an agent (e.g., an agent identified by a screening assay described herein), or combination of agents that modulates (e.g., up regulates or down regulates) 33945 expression or activity. In another embodiment, the method involves administering a 33945 protein or nucleic acid molecule as therapy to compensate for reduced, aberrant, or unwanted 33945 expression or activity.

Stimulation of 33945 activity is desirable in situations in which 33945 is abnormally downregulated and/or in which increased 33945 activity is likely to have a beneficial effect. For example, stimulation of 33945 activity is desirable in situations in which a 33945 is downregulated and/or in which increased 33945 activity is likely to have a beneficial effect. Likewise, inhibition of 33945 activity is desirable in situations in which 33945 is abnormally upregulated and/or in which decreased 33945 activity is likely to have a beneficial effect.

Pharmacogenomics

The 33945 molecules of the present invention, as well as agents, or modulators which have a stimulatory or inhibitory effect on 33945 activity (e.g., 33945 gene expression) as identified by a screening assay described herein can be administered to individuals to treat (prophylactically or therapeutically) 33945 associated disorders (e.g., protein glycosylation, cellular adhesion, atherosclerosis, endothelial cell disorders, cellular proliferation or differentiation disorders) associated with aberrant or unwanted 33945 activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 33945 molecule or 33945 modulator as well as tailoring the dosage and/or therapeutic regimen of treatment with a 33945 molecule or 33945 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23:983–985 and Linder, M. W. et al. (1997) Clin. Chem. 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 33945 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 33945 molecule or 33945 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 33945 molecule or 33945 modulator, such as a modulator identified by one of the exemplary screening assays described herein.

The present invention further provides methods for identifying new agents, or combinations, that are based on identifying agents that modulate the activity of one or more of the gene products encoded by one or more of the 33945 genes of the present invention, wherein these products can be associated with resistance of the cells to a therapeutic agent. Specifically, the activity of the proteins encoded by the 33945 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 33945 protein can be applied in clinical trials. For example, the effectiveness of an agent determined by a screening assay as described herein to increase 33945 gene expression, protein levels, or upregulate 33945 activity, can be monitored in clinical trials of subjects exhibiting decreased 33945 gene expression, protein levels, or downregulated 33945 activity. Alternatively, the effectiveness of an agent determined by a screening assay to decrease 33945 gene expression, protein levels, or downregulate 33945 activity, can be monitored in clinical trials of subjects exhibiting increased 33945 gene expression, protein levels, or upregulated 33945 activity. In such clinical trials, the expression or activity of a 33945 gene, and preferably, other genes that have been implicated in, for example, a glycosyltransferase-associated or another 33945-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 33945 or from a cell or subject in which a 33945 mediated response has been elicited; contacting the array with a 33945 nucleic acid (preferably purified), a 33945 polypeptide (preferably purified), or an anti-33945 antibody, and thereby evaluating the plurality of capture probes. Binding, e.g., in the case of a nucleic acid, hybridization with a capture probe at an address of the plurality, is detected, e.g., by a signal generated from a label attached to the 33945 nucleic acid, polypeptide, or antibody.

The capture probes can be a set of nucleic acids from a selected sample, e.g., a sample of nucleic acids derived from a control or non-stimulated tissue or cell.

The method can include contacting the 33945 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 33945. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 33945, e.g., analyzing structure, function, or relatedness to other nucleic acid or amino acid sequences. The method includes: providing a 33945 nucleic acid or amino acid sequence; comparing the 33945 sequence with one or more preferably a plurality of sequences from a collection of sequences, e.g., a nucleic acid or protein sequence database; to thereby analyze 33945.

The method can include evaluating the sequence identity between a 33945 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 33945. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 33945 molecules are provided in a variety of mediums to facilitate use thereof. A sequence can be provided as a manufacture, other than an isolated nucleic acid or amino acid molecule, which contains a 33945 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 33945 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 33945 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 33945 sequence information.

A variety of data storage structures are available to a skilled artisan for creating a computer readable medium having recorded thereon a 33945 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 33945 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a glycosyltransferase-associated or another 33945-associated disease or disorder or a pre-disposition to a glycosyltransferase-associated or another 33945-associated disease or disorder, wherein the method comprises the steps of determining 33945 sequence information associated with the subject and based on the 33945 sequence information, determining whether the subject has a glycosyltransferase-associated or another 33945-associated disease or disorder and/or recommending a particular treatment for the disease, disorder, or pre-disease condition.

The present invention further provides in an electronic system and/or in a network, a method for determining whether a subject has a glycosyltransferase-associated or another 33945-associated disease or disorder or a pre-disposition to a disease associated with 33945, wherein the method comprises the steps of determining 33945 sequence information associated with the subject, and based on the 33945 sequence information, determining whether the subject has a glycosyltransferase-associated or another 33945-associated disease or disorder or a pre-disposition to a glycosyltransferase-associated or another 33945-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a glycosyltransferase-associated or another 33945-associated disease or disorder or a predisposition to a glycosyltransferase-associated or another 33945-associated disease or disorder, said method comprising the steps of receiving 33945 sequence information from the subject and/or information related thereto, receiving phenotypic information associated with the subject, acquiring information from the network corresponding to 33945 and/or corresponding to a glycosyltransferase-associated or another 33945-associated disease or disorder, and based on one or more of the phenotypic information, the 33945 information (e.g., sequence information and/or information related thereto), and the acquired information, determining whether the subject has a glycosyltransferase-associated or another 33945-associated disease or disorder or a pre-disposition to a glycosyltransferase-associated or another 33945-associated disease or disorder. The method may further comprise the step of recommending a particular treatment for the disease, disorder, or pre-disease condition.

The present invention also provides a business method for determining whether a subject has a glycosyltransferase-associated or another 33945-associated disease or disorder or a pre-disposition to a glycosyltransferase-associated or another 33945-associated disease or disorder, said method comprising the steps of receiving information related to 33945 (e.g., sequence information and/or information related thereto), receiving phenotypic information associated with the subject, acquiring information from the network related to 33945 and/or related to a glycosyltransferase-associated or another 33945-associated disease or disorder, and based on one or more of the phenotypic information, the 33945 information, and the acquired information, determining whether the subject has a glycosyltransferase-associated or another 33945-associated disease or disorder or a pre-disposition to a glycosyltransferase-associated or another 33945-associated disease or disorder. The method may further comprise the step of recommending a particular treatment for the disease, disorder, or pre-disease condition.

The invention also includes an array comprising a 33945 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 33945. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a glycosyltransferase-associated or another 33945-associated disease or disorder, progression of glycosyltransferase-associated or another 33945-associated disease or disorder, and processes, such a cellular transformation associated with the glycosyltransferase-associated or another 33945-associated disease or disorder.

The array is also useful for ascertaining the effect of the expression of a gene on the expression of other genes in the same cell or in different cells (e.g., acertaining the effect of 33945 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 33945) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 33945 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 33945 sequence, or record, in computer readable form; comparing a second sequence to the 33945 sequence; thereby analyzing a sequence. Comparison can include comparing to sequences for sequence identity or determining if one sequence is included within the other, e.g., determining if the 33945 sequence includes a sequence being compared. In a preferred embodiment the 33945 or second sequence is stored on a first computer, e.g., at a first site and the comparison is performed, read, or recorded on a second computer, e.g., at a second site. E.g., the 33945 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

The contents of all references, patents and published patent applications cited throughout this application are incorporated herein by reference. This invention is further illustrated by the following exemplification, which should not be construed as limiting.

Exemplification

Gene Expression Analysis Survey

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPTTM Choice System following the manufacturer's instructions (GibcoBRL). A negative control of RNA without reverse transcriptase was mock reverse transcribed for each RNA sample.

Human 33945 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 33945 gene. Each human 33945 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for p-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 33945 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 33945 gene is normalized by subtracting the Ct value of the β-2 microglobulin gene to obtain a $_\Delta$Ct value using the following formula: 66 Ct=Ct$_{human\ 59914\ and\ 59921}$–Ct$_{\beta-2\ microglobulin}$. Expression is then calibrated against a cDNA sample showing a comparatively low level of expression of the human 33945 gene. The $_\Delta$Ct value for the calibrator sample is then subtracted from $_\Delta$Ct for each tissue sample according to the following formula: $_{\Delta\Delta}$Ct=$_\Delta$Ct-$_{sample}$-$_\Delta$Ct-$_{calibrator}$. Relative expression is then calculated using the arithmetic formula given by $2^{-\Delta\Delta Ct}$. Expression of the target human 33945 gene in each of the tissues tested is then graphically represented as discussed in more detail below.

The results indicate that 33945 mRNA is expressed at high levels in coronary smooth muscle cells and pancreas. In addition, there are differential levels of expression between tumors and their corresponding normal tissue, e.g. a high level of 33945 expression in colon tumor with a medium amount of expression in normal colon; a medium amount of 33945 expression in lung tumor tissue, and a low amount in normal lung. Further tests of 33945 expression found significant expression in situations characteristic of high amounts of angiogenesis, e.g., in fetal kidney, in Wilm's tumor of the kidney and in squamous cell carcinoma of the cervix. Medium amounts of 33945 expression also were found in kidney, brain cortex, inflammatory bowel disease colon tissue, and normal small intestine. Small amounts of 33945 expression also were found in normal artery, diseased aorta, human umbilical vein endothelial cells, skeletal muscle, breast tumor, prostate tumor, chronic obstructive pulmonary disease lung tissue, decubitus skin tissue, and megakaryocytes. Trace amounts of 33945 expression also were found in hemangioma, congestive heart failure heart tissue, normal adipose, normal spinal cord, differentiated osteoclasts, hypothalamus, normal breast, normal prostate, normal lymph node, normal tonsil, synovium, and activated peripheral blood monocytes.

33945 Gene Expression Analysis after Interferon Gamma Treatment

Cultured human cardiac microvascular endothelial cells (Clonetics) were treated for various times with 100 ng/ml interferon gamma. Total RNA was extracted and analyzed for 33945 expression by TaqMan® quantitative PCR as described above. A gene which does not respond to interferon gamma, psmd, was used as an internal control. Relative to the control without interferon gamma, 33945 expression had insignificant change in expression after 1 hour or 5 hours of interferon gamma treatment (86.6 versus 79.6 and 84.6 versus 75.4 expression units, respectively), but had significantly increased expression after 24 hours of interferon gamma treatment (164.7 versus 70.6 expression units).

33945 Gene Expression in Proliferating Endothelial Cells

The expression of 33945 was analyzed in endothelial cell cultures during different phases of growth. Total RNA was extracted and analyzed for 33945 expression by TaqMan® quantitative PCR as described above. Rapidly proliferating human umbilical vein endothelial cells and human cardiac microvascular endothelial cells had higher levels of expression of 33945 than their corresponding confluent, quiescent cells (1.5 versus 0.075 and 0.25 versus 0.035 expression units, respectively).

Equivalent

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule or a complement thereof selected from the group
   a) a nucleic acid molecule which encodes a polypeptide comprising an amino acid sequence with at least 95% identity to the amino acid sequence of SEQ ID NO:2, wherein said polypeptide has a glycosyltransferase activity;
   b) a nucleic acid molecule which encodes a polypeptide consisting of fragment of SEQ ID NO:2, wherein the fragment comprises at least 285 contiguous amino acids of SEQ ID NO: 2, wherein said at least 285 contiguous amino acids comprise the glycosyltransferase domain of 33945 (amino acids 139 to 322 of SEQ ID NO:2), and the fragment has a glycosyltransferase activity; and
   c) a nucleic acid molecule which encodes a naturally occurring allelic variant of a polypeptide comprising the amino acid sequence of SEQ ID NO:2, wherein the nucleic acid molecule hybridizes to a nucleic acid molecule comprising SEQ ID NO: 1, 3, or a complement thereof, under hybridization conditions of 0.5 M sodium phosphate, 7% SDS at 65° C., followed by one or more washes at 0.2×SSC, 1% SDS at 65° C., wherein said nucleic acid molecule encodes a polypeptide having a glycosyltransferase activity.

2. An isolated nucleic acid molecule selected from the group consisting of:
   a) a nucleic acid molecule comprising the nucleotide sequence of SEQ ID NO:1, SEQ ID NO:3; and
   b) a nucleic acid molecule which encodes a polypeptide comprising the amino acid sequence of SEQ ID NO:2.

3. The nucleic acid molecule of claim 1 further comprising vector nucleic acid sequences.

4. The nucleic acid molecule of claim 1 further comprising nucleic acid sequences encoding a heterologous polypeptide.

5. A recombinant host cell which contains the nucleic acid molecule of claim 1.

6. The recombinant host cell of claim 5 which is a mammalian recombinant host cell.

7. A non-human mammalian recombinant host cell containing the nucleic acid molecule of claim 1.

8. A method for producing a 33945 polypeptide selected from the group consisting of:
   a) a polypeptide comprising an amino acid sequence with at least 95% identity to the amino acid sequence of SEQ ID NO:2, wherein said polypeptide has a glycosyltransferase activity;

b) a polypetride consisting of a fragment of the amino acid sequence of SEQ ID NO:2, wherein the fragment comprises at least 285 contiguous amino acids of SEQ ID NO:2, wherein said at least 285 contiguous amino acids comprise the glycosyltransferase domain of 33945 (amino acids 139 to 322 of SEQ ID NO:2), and the fragment has a glycosyltransferase activity; and c) a polypeptide comprising a naturally occurring allelic variant of a polypeptide comprising the amino acid sequence of SEQ ID NO:2, wherein the polypeptide is encoded by a nucleic acid molecule which hybridizes to a nucleic acid molecule comprising SEQ ID NO:1, SEQ ID NO:3, or a complement thereof under hybridization conditions of 0.5 sodium phosphate, 7% SDS at 65° C., followed by one or more washes at 0.2×SSC, 1% SDS at 65° C., wherein said polypeptide has a glycosyltransferase activity;

comprising culturing the host cell of claim 5 under conditions in which the nucleic acid molecule is expressed.

9. A kit comprising the isolated nucleic acid molecule of claim 1 and instructions for use.

10. A recombinant host cell which expresses the nucleic acid molecule of claim 1.

11. The recombinant host cell of claim 10 which is a mammalian recombinant host cell.

12. An isolated nucleic acid molecule, consisting of a nucleic acid sequence selected from the group consisting of:

a) SEQ ID NO:1;

b) SEQ ID NO:3; and c) a nucleic acid molecule which encodes a polypeptide having an amino acid sequence consisting of SEQ ID NO:2.

13. The isolated nucleic acid molecule of claim 1, wherein the nucleic acid molecule encodes a polypeptide comprising an amino acid sequence with at least 98% identity to the amino acid sequence of SEQ ID NO:2, wherein said polypeptide has a glycosyltransferase activity.

14. A recombinant host cell which expresses the nucleic acid molecule of claim 12.

15. A recombinant host cell which expresses the nucleic acid molecule of claim 2.

16. The nucleic acid molecule of claim 2, further comprising vector nucleic acid sequences.

17. The nucleic acid molecule of claim 2, further comprising nucleic acid sequences encoding a heterologous polypeptide.

18. The method of claim 8, wherein the polypeptide comprises SEQ ID NO:2.

19. The method of claim 8, wherein the polypeptide is a fusion protein linked to a non-33945 polypeptide.

* * * * *